(12) United States Patent
Vidal et al.

(10) Patent No.: US 6,778,910 B1
(45) Date of Patent: Aug. 17, 2004

(54) STATISTICAL PROBABILITY DISTRIBUTION-PRESERVING ACCUMULATION OF LOG TRANSFORMED DATA

(75) Inventors: Patricio Vidal, Miami, FL (US); John S. Riley, Miami, FL (US); Malek Adjouadi, Miami, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 10/375,845

(22) Filed: Feb. 26, 2003

(51) Int. Cl.[7] .............................................. G01N 33/48
(52) U.S. Cl. .............................. 702/21; 702/19; 702/30; 702/187
(58) Field of Search ............................. 702/21, 19, 22, 702/30, 20, 187; 382/128; 73/865.5

(56) References Cited

U.S. PATENT DOCUMENTS 6,014,904 A * 1/2000 Lock ........................ 73/865.5

2003/0036855 A1 * 2/2003 Harris et al. .................. 702/19

* cited by examiner

*Primary Examiner*—John Barlow
*Assistant Examiner*—Hien Vo
(74) *Attorney, Agent, or Firm*—Charles E. Wands; Mitchell E. Alter

(57) ABSTRACT

A signal processing operator successfully expands the dynamic range of a histogram of digital data, such as that representative of biological cell populations, including human blood cells subjected to flow cytometry processing, without introducing binning artifacts into the transformed data. The inventive data mapping scheme effectively preserves statistical probability distribution characteristics of the original data, that would otherwise be removed or lost in the course of expanding the dynamic range of a quantized histogram data set through the use of a conventional log transformation. Filtering is unnecessary, as the binning effect is countered early in the process, to preserve statistical properties of the cell populations under study.

20 Claims, 22 Drawing Sheets

STATISTICAL PROBABILITY DISTRIBUTION-PRESERVING ACCUMULATION OF LOG TRANSFORMED DATA

FIELD OF THE INVENTION

The present invention relates in general to statistical analysis of one or more data sample distributions, such as a histogram of photoluminescence data produced by a blood flow cytometer system, and is particularly directed to a signal processing operator that is operative to preserve statistical probability distribution characteristics for a quantized data set that is subjected to a dynamic range expansion transform, such as a logarithmic operator, which, without the statistical probability preservation mechanism, would introduce undesirable binning artifacts into the transformed data.

BACKGROUND OF THE INVENTION

Flow cytometry derives from the quantitative measurement (meter) of structural features of biological cells (cyto) transported by a carrier in a controlled flow through a series of primarily optical detectors. Flow cytometers have been commercially available since the early 1970's, and their use has been continuously increasing. The most numerous flow cytometers are those employed for complete blood cell counts in clinical laboratories. Flow cytometers are found in all major biological research institutions. They are also numerous in medical centers, where they are used for diagnosis as well as research. There are currently on the order of 7,000 flow cytometers in use worldwide. Chromosome count and cell cycle analysis of cancers is the major diagnostic use. Lymphomas and leukemia are intensively studied for surface markers of diagnostic and prognostic value. Flow cytometry,has been the method of choice for monitoring AIDs patients.

The general architecture of a flow cytometer system is shown diagrammatically in FIG. 1(a). Cells in suspension (retained in a saline carrier reservoir 10) are caused to flow one at a time (typically at rates of over 100 cells per second) through a transport medium 12 (such as a capillary tube 12). As the stream of cells flows through the capillary, the cells pass through an illumination region or window 14, one at the time, where they are illuminated by a focused optical output beam produced by a laser 16. Distributed around the illumination window are a plurality of optical sensors 18, that are located so as to intercept and measure the optical response of each cell to the laser beam illumination, including forward scatter intensity (proportional to cell diameter), orthogonal scatter intensity (proportional to cell granularity), and fluorescence intensities at various wavelengths. Each optical sensor's measurement output is then digitized and coupled to a computer (signal processor) 20 for processing.

Because different cell types can be differentiated by the statistical properties of their measurements, flow cytometry can be use to separate and count different cell populations in a mixture (blood sample, for example). In addition, the cells can be stained with fluorescent reagents or dyes that bind to specific biochemical receptors of certain cells, allowing the measurement of biological and biochemical properties. The object of flow cytometry is to separate and quantify cell populations. Typically, the acquired data is accumulated into one or two dimensional data distributions so that the morphological variability of the distributions can be interpreted to distinguish the cellular populations.

In the current approaches for analyzing flow cytometric histograms, a pre-processing step known as the log-transformation, is employed to increase the dynamic range of the data distribution, in order to facilitate analysis and henceforth enhance interpretation. Unfortunately, although this step serves to broaden the dynamic range of the data distributions, it introduces an undesirable artifact, known as the "picket fence" or "binning effect", that undermines the one aspect of the solution it is intended to reinforce.

This may be illustrated by reference to FIGS. 1(b) and 1(c), wherein FIG. 1(b) shows two overlapped Gaussian distributions as the original data, and FIG. 1(c) shows in discontinuous vertical bold black lines the binning or picket fence effect in the histogram of the log-transformed data; the continuous gray line in FIG. 1(c) is the ideal continuous transformation. This transformation data is beset with contentious aspects. Even if dynamically expanded, it introduces a significant binning artifact; moreover, the result from the discrete log transformation is not suitable for data analysis or any direct and consequential statistical analysis.

In an effort to counter the binning effect's undesired artifacts, which skew the analysis/interpretation of the results, a number of practitioners have relied upon filtering techniques, that attempt to attenuate this undesired effect without introducing changes that might undermine the statistical values of the original data. However, these filtering approaches are fraught with an irreconcilable issues: that of relating the degree to which the artifact must be filtered with the point at which the filtered data is still considered to retain statistics similar to the original data.

More particularly, to resolve the binning effect issue, averaging schemes based on finite impulse response (FIR) filters are typically used. Most effective FIR filtering schemes are achieved using a traditional (1-2-1) 3-tap FIR filter. Such a filter has have positive attributes, provided that the following constraints are met: 1-maintaining the area under the curve requires that the sum of the FIR filter coefficients equals 1, and that the appropriate boundary conditions have been met; 2- to prevent the data from being skewed, the filter coefficients must be symmetric around the center (this requires that the number of filter taps in the FIR filter be odd), and the individual distributions must be symmetrical and not overlapping, which is not typically true when analyzing log-transformed data from cell populations.

FIGS. 2(a), 2(b), 2(c) and 2(d) respectively illustrate the effects of an FIR filtering scheme, after 20, 100, 200 and 500 passes of the binned histogram of FIG. 1(c) through a traditional (1-2-1) FIR filter. In each of these Figures, the bold black curve is the filtered histogram, while the gray curve shows the ideal transformed data. From qualitative analyses of the results of the FIR smoothing, one might infer that there is an optimal number of passes required for the closest approximation to the actual distribution. However, FIR filtering cannot be optimal, because the log transformation function has been applied to initially Gaussian populations, and the resultant log-normal populations will be skewed. Clearly, after 500 passes, this can be observed. Another factor that makes the use of FIR filtering techniques inappropriate is the fact that, depending on the physical properties of the cells and the particular sensors used, the cell populations may overlap, and therefore any excessive filtering will skew their statistical properties.

Other practitioners have attempted to ameliorate the binning effect by making use of log-amplifiers to electronically transform the input signal in its analog form before digitalization. This approach has a number of drawbacks: 1- it requires the use of additional and expensive hardware; 2- logarithmic amplifiers are notoriously noisy and unstable; and 3- when linear data is also required, the instruments must send and store twice the amount of data.

Another proposal to overcome the binning effect is to use high-resolution analog-to-digital converters (ADCs), in an effort to prevent the log transformation from exhibiting discontinuities in the lower range histogram channels. This approach is not perfect and has the following problems: 1- high-resolution ADCs converters are expensive; 2- the amount of data the instruments must send and store will increase proportionally with the increase in bit resolution of the ADC—another expensive proposition; and 3- no matter what the resolution of the ADC converter used, the binning effect, although minimized, will still be present in the output histogram. Of course, there is a point where the natural irregularities of the real data will be greater than the binning effect.

SUMMARY OF THE INVENTION

In accordance with the present invention, the above drawbacks of conventional signal processing mechanisms used to process histograms of data, especially data associated with biological cell populations, including human blood cells that have been subjected to flow cytometry processing, are effectively obviated by a new and improved, statistical probability distribution-preserving histogram transform mechanism. This inventive mechanism effectively preserves the statistical probability distribution characteristics of the original data that would otherwise be removed or lost in the course of expanding the dynamic range of a quantized histogram data set through the use of a conventional log transformation. With this new approach to data mapping, the need for filtering becomes a non-issue, since the binning effect is countered early in the process, thus preserving the statistical properties of populations under study.

As will be detailed hereinafter, the present inventors have determined that the binning effect results from the erroneous premise that an input data range [x0, x0+1) uniformly maps or is transformed to the output data range [t(x0), t(x0)+1), where t(x) is the transformation function. In actuality, however, when mapping digitized input data to the transformed domain, the quantization or discretization process carried out by an analog-to-digital converter implements a floor function, so that for the analog data range [x0, x0+1), the output will be the integer digital value x0.

If the probability distribution of the input data sample in the range [x0, x0+1) is known, then the probability distribution in the transformed domain can be determined. When input data is transformed from the input domain, X, to the output domain, Y, using a given transformation Y=t(X), the input probability distribution, $f_X(x)$, is transformed into $f_Y(y)$. Because the transformation does not affect the probability of each event, the infinitesimal probability of any point x is the same at the output value y=t(x). In mathematical terms this may be expressed as $f_Y(y)*dy=f_X(x)*dx$. By manipulation and substituting x by $t^{-1}(y)$, the relationship between the resulting probability distribution, $f_Y(y)$, and the input probability distribution, $f_X(x)$, may be expressed as $f_Y(Y)=f_X(t^{-1}(y))*d/dy(t^{-1}(y))$, where X and Y are two random variables related by the transformation Y=t(x), and t(x) is a monotonically increasing transformation function whose inverse $t^{-1}(y)$ has a continuous derivative on Y. This ensures that the areas under the input and output probability distributions are maintained—an important requisite when analyzing cell populations.

For a typical log transformation, the transformed density distribution may be expressed as: $g(y)=f(K*e^{y/s})*K*S*e^{y/s}$, where S and K are scaling constants defined as S=D/(B−1) and $K=2^R/10^D$, B is the number of bins in the output histogram, D is the number of desired decades, and R is the bit resolution of the ADC converter. In order to employ this transformed log density distribution expression, it is necessary to know the probability distribution of the input histogram, which is unknown, but can be approximated.

The binning effect may be considered to be the result of assuming that the input probability distribution at each ADC interval is a delta function positioned at each ADC output value. In actuality, however, this erroneous assumption is the least probable case when dealing with biological events, such as biological cell populations. To improve the accuracy of the log-transformation, a more realistic probability distribution at each ADC interval, such as uniform approximation, linear approximation, and any upper order approximation, may be used.

When using a uniform approximation, the probability distribution of the input data in each ADC interval is assumed to be uniform. Analysis has shown that the resulting histogram more closely resembles the ideal transformation, as binning effect artifacts are eliminated. In addition, although is not an ideal transformation, the area under the curve is maintained. The uniform approximation can be readily implemented in real-time using look-up tables. Although the uniform approximation provides results similar to the ideal transformation, imperfections may occur in the lower range at the locations of the holes of the binned histogram, as a direct result of the difference between the actual input distribution and the uniform approximation made. To improve upon the results obtained with the uniform approximation a higher order approximation, such as a linear approximation, may be employed.

As its name implies, when a linear approximation is used, the probability distribution of the input data in each ADC interval is assumed to be linear. Analysis has shown that the results are practically identical to the ideal log-transformation, and the area under the curve is again maintained. Although results can be improved using higher approximations, it does not make practical sense to do so, since the natural variability of biological populations is likely to be far greater than the error of the approximation made.

Because the amplitudes of the output histogram are non-integer, it is impossible to create a sequence of data values that generates the same output histogram. This also makes it impossible to directly enumerate cell populations, on an event by event basis, based on analysis of the output histogram; however, this is easily overcome by performing an inverse transformation of analysis results into the input domain and enumerating cell populations using input events.

In order to implement the signal processing operator of the invention in real time in a flow cytometer, it is necessary to process each data point as it is being acquired, or process all of the data after acquisition. Namely, the objective is to accumulate the histogram as the data points are acquired. Using the above log-transformed density distribution expression, and assuming that the probability distribution for any given input data range [x0, x0+1) is uniform, a non-integer bin or channel contribution in the output histogram can be computed by applying this expression to each input data point. The bin/channel contributions are then summed to form the output histogram.

Because the output histogram bins have integer boundaries, the area under the ideal curve in each bin is computed and assigned to that bin. The total area of the resulting non-integer bin contributions sum to a value of one. Adjacent data ranges produce overlapping contributions, which serve to fill in adjacent areas, namely, there is an effective "spreading" of one input data point into several non-integer bins that fill in the discontinuities or "holes" and eliminate the "spikes" observed in a typical binned histogram.

Different types of non-integer bin contributions for the log transformation are computed and accumulated for each data point being mapped from the original domain to the transformed domain. Each set of bin contributions is different and is a function of the position of the histogram channel. This may be readily implemented using look-up tables. A relatively fast way to accumulate the histogram is to have pre-computed in memory all necessary non-integer bin contributions indexed by input channel. These pre-computed values can then be used as a look-up table to provide fast access to the information. The non-integer contributions are described so as to allow for efficient retrieval from memory and adding them to the output histogram. The use of pre-computed look-up tables makes computation time inconsequential, allowing the invention to be implemented effectively in real-time.

DETAILED DESCRIPTION

Figure 1:
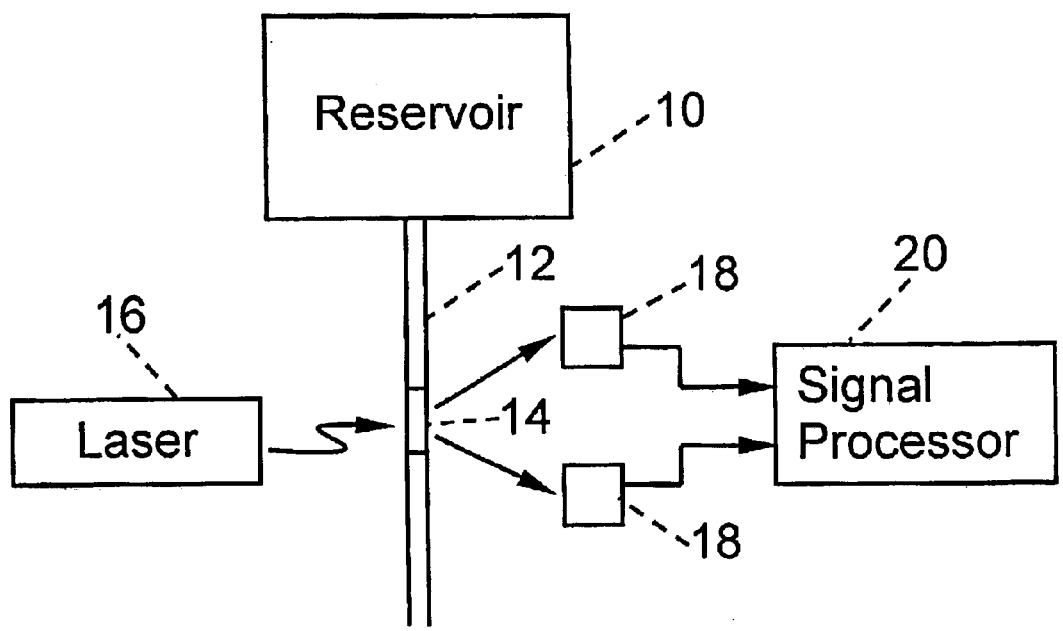
FIG. 1(a) diagrammatically illustrates the general architecture of a flow cytometer system.
FIG. 1(b) shows two overlapped Gaussian distributions of cytometer data.
FIG. 1(c) shows in the gray curve the ideal continuous log transform of the data of FIG. 1(b), and in the black curve the binning effect produced by a log transform of the histogram of the data of FIG. 1(b)

Before detailing the statistical probability distribution-based histogram transform mechanism in accordance with the present invention, it should be observed that the invention resides primarily in what is effectively a software-based signal processing tool employed by a data analysis processor, such as a flow cytometry cell population analyzer, that is effective to perform an expansion of the dynamic range of cell distribution data without introducing 'binning' artifacts into the transformed data.

Consequently, the invention and a flow cytometer environment in which it may be employed have been illustrated in the drawings by readily understandable block diagrams and histogram transform graphs, which show only those specific details that are pertinent to the present invention, so as not to obscure the disclosure with details which will be readily apparent to those skilled in the art having the benefit of the description herein. Thus, the Figures are primarily intended to illustrate the major components and transform operators of which the invention is comprised in convenient functional groupings, whereby the present invention may be more readily understood.

In order to facilitate an appreciation of the statistical probability preservation-based signal processing mechanism of the present invention, and the manner in which it effectively obviates the binning effect in a dynamic range-expanded quantized data distribution, it is initially useful to more closely examine the exact behavior of the binning effect, and what gives rise to it.

Figure 3:
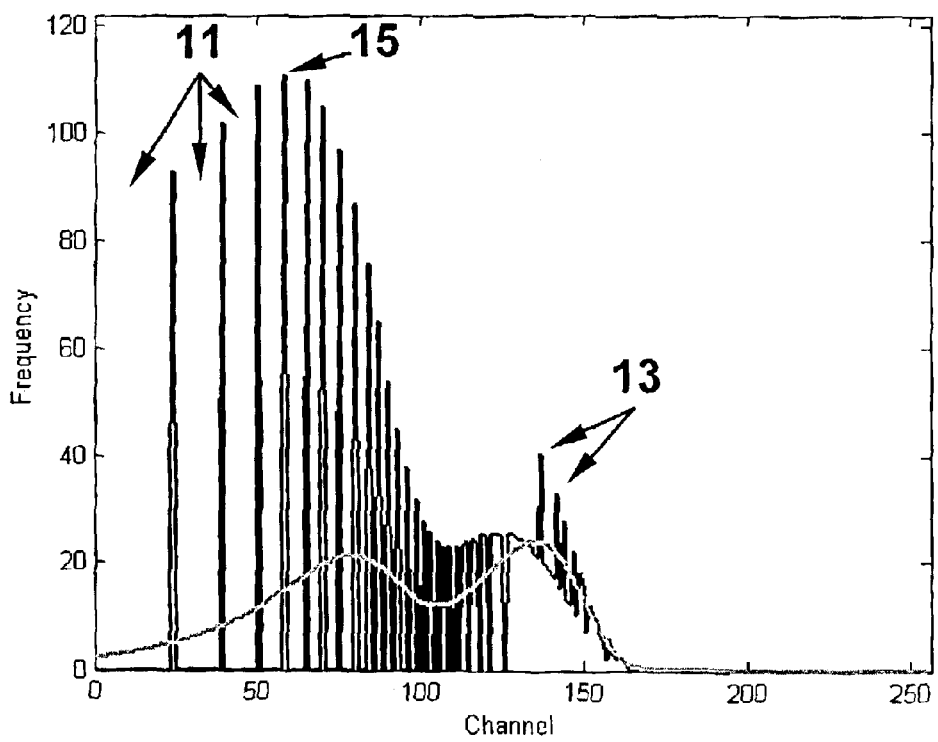
FIG. 3 corresponds to FIG. 1(c) with additional numerical identifiers associated with spikes and holes in the discontinuous log-transformed histogram.

As described above with reference to FIGS. 1(b) and 1(c), and as numerically identified in FIG. 3 (which corresponds to FIG. 1(c)), when logarithmically transformed data is accumulated into a frequency histogram with a finite number of channels (or bins), several major, and very visible, artifacts are produced. These include "holes" 11 in the transformed histogram, wherein some of the low histogram channels are not accumulated, although the input data is continuous, and "spikes" 13, where data is compressed in the high histogram channels in a non-uniform manner. In addition, there are "higher peak amplitudes" 15, where the peak values of the low histogram channels are artificially enlarged.

Equation (1) is an example of a standard logarithmic transformation that is commonly used in flow cytometry:

$$t(x)=\log(x/K)/S \qquad (1)$$

where $t(x)$ is the output transformed value, x is the input value, S and K are scaling constants defined as $S=D/(B-1)$ and $K=2^R/10^D$, B is the number of bins in the output histogram, D is the number of desired decades, and R is the bit resolution of the ADC converter.

This Equation maps input data x from the full resolution of the ADC converter to the desired number of channels in the output histogram.

Figure 4:
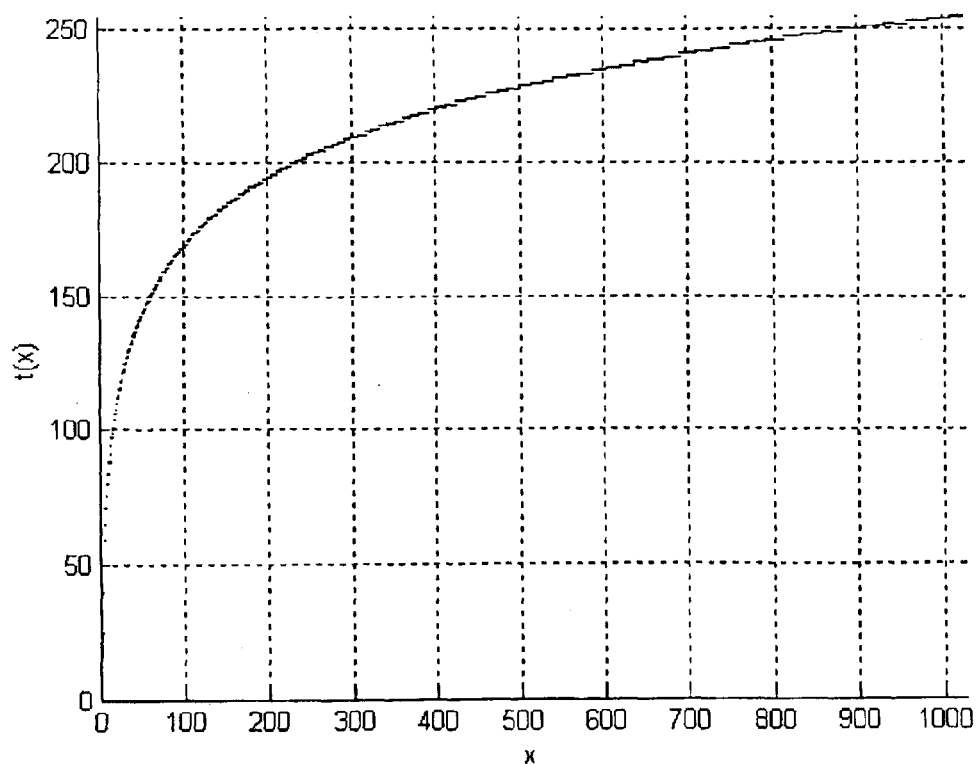
FIG. 4 is a graphical realization of the log transformation of Equation (1) for an ADC input resolution of 10 bits, 3 decades, and an output histogram of 256 channels.
Figure 5A:
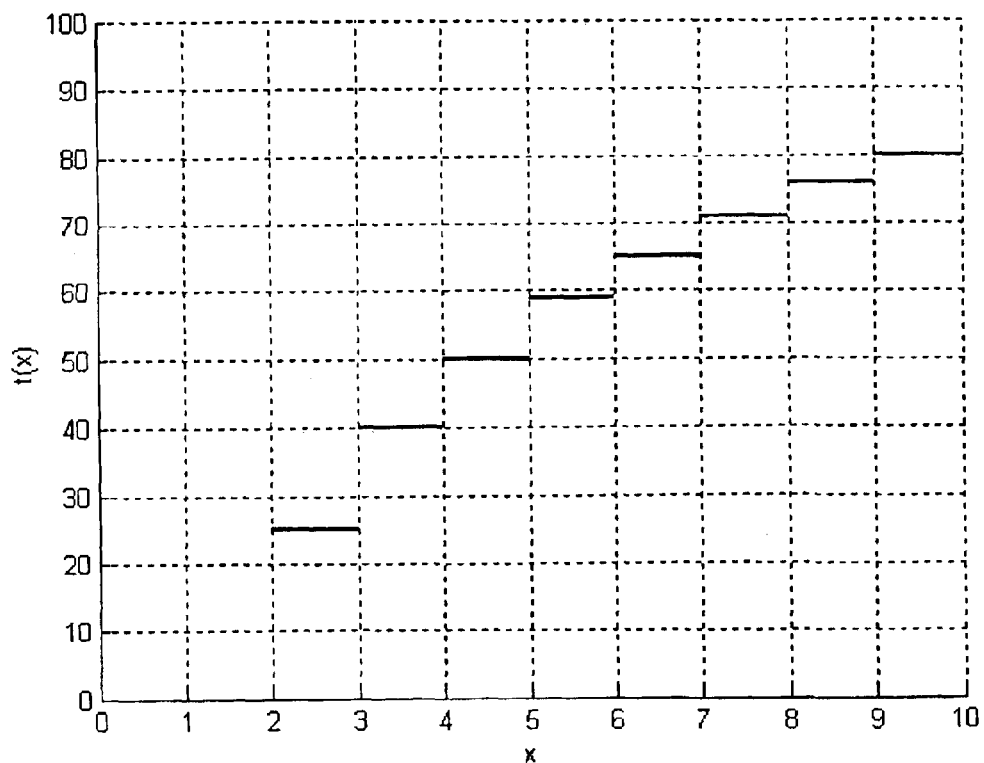
FIG. 5(a) shows a lower range portion of FIG. 4 showing how consecutive input data values would be mapped to non-consecutive channels.
Figure 5B:
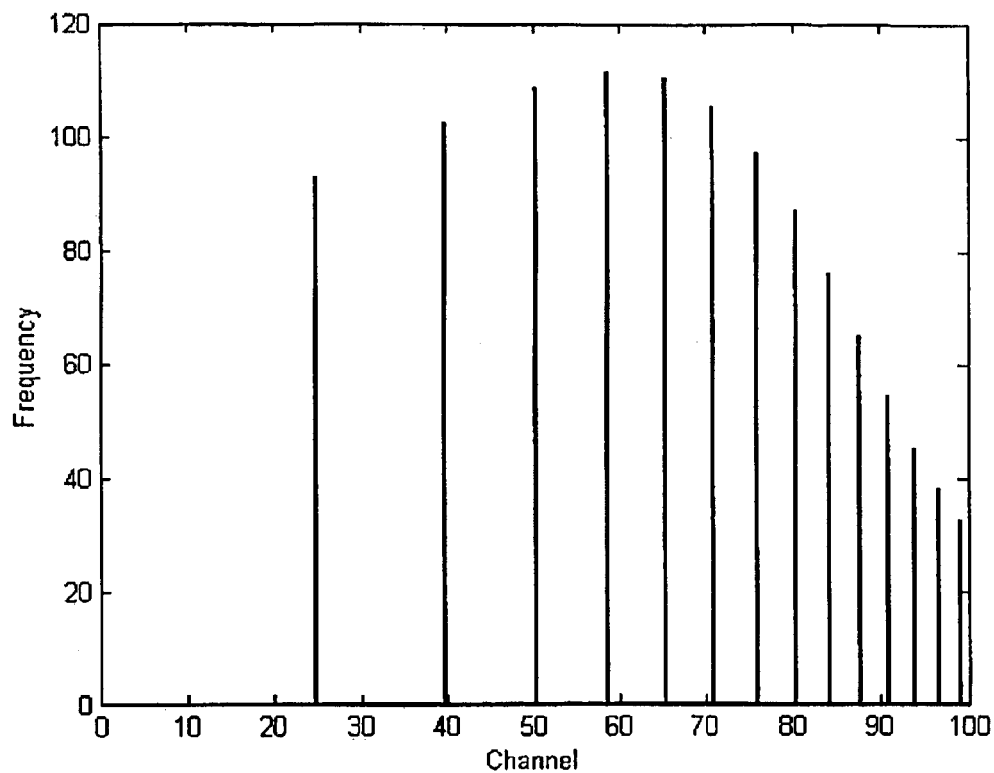
FIG. 5(b) shows "holes" in the log-transformed histogram of FIG. 5(a) at channels where the log-transformation does not provide a direct mapping.

FIG. 4 shows the realization of the log transformation of Equation (1) for an input bit resolution of 10 bits, 3 decades, and an output histogram of 256 channels. In the lower range of the logarithmic transformation, the input data is expanded such that consecutive input data values are mapped to non-consecutive channels, as shown in FIG. 5(a). In this figure consecutive input data values 1 and 2 are mapped to channels 0 and 25, respectively, consecutive input data values 2 and 3 are mapped to channels 25 and 40, respectively, and so on, for all subsequent data points in the lower range. As described above, and shown in FIG. 5(b), "holes" are created at those channels in the output histogram where the log-transformation does not provide direct mapping.

Figure 6A:
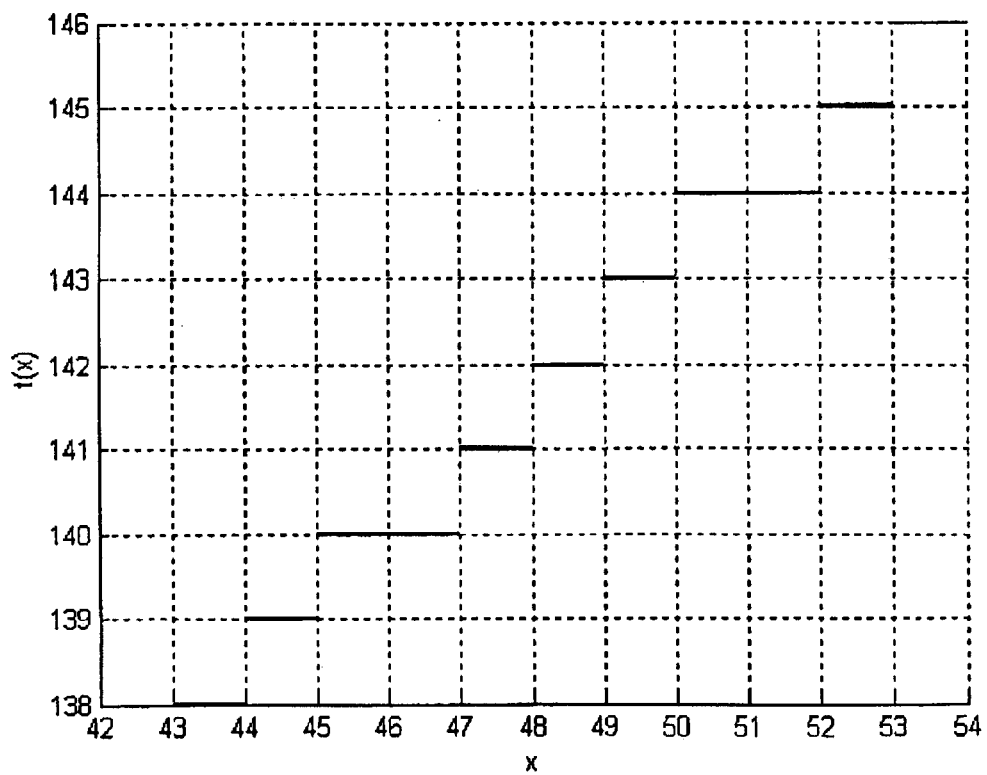
FIG. 6(a) illustrates how consecutive input data values would be mapped in the middle range channels of a log-transformed histogram.
Figure 6B:
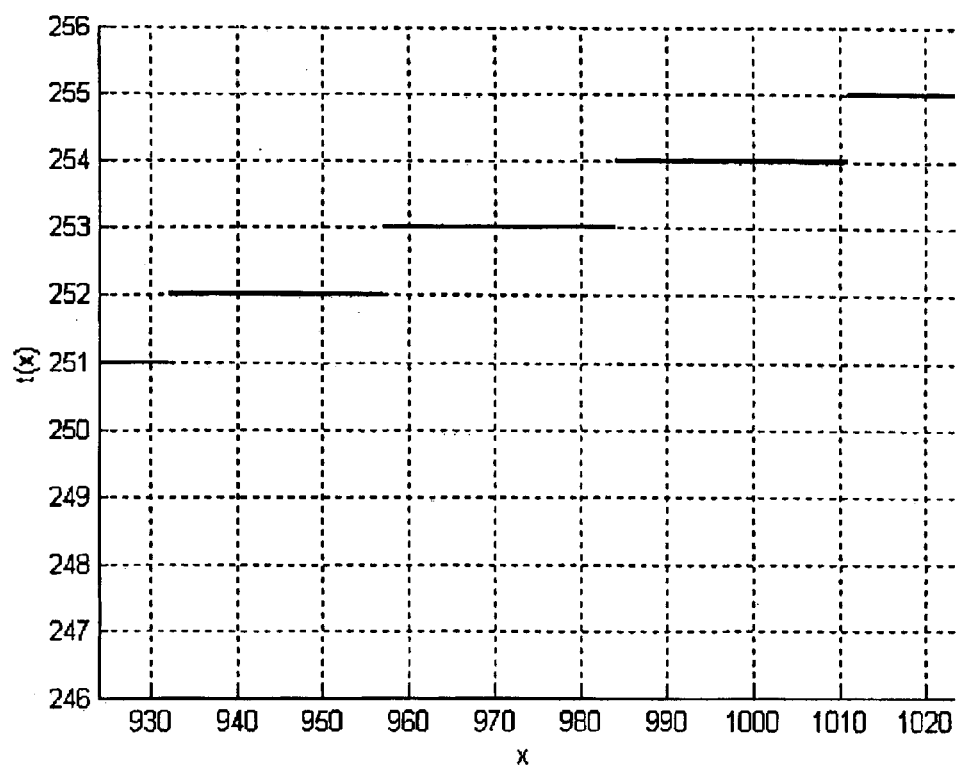
FIG. 6(b) illustrates how consecutive input data values would be mapped in the upper range channels of a log-transformed histogram.
Figure 7A:
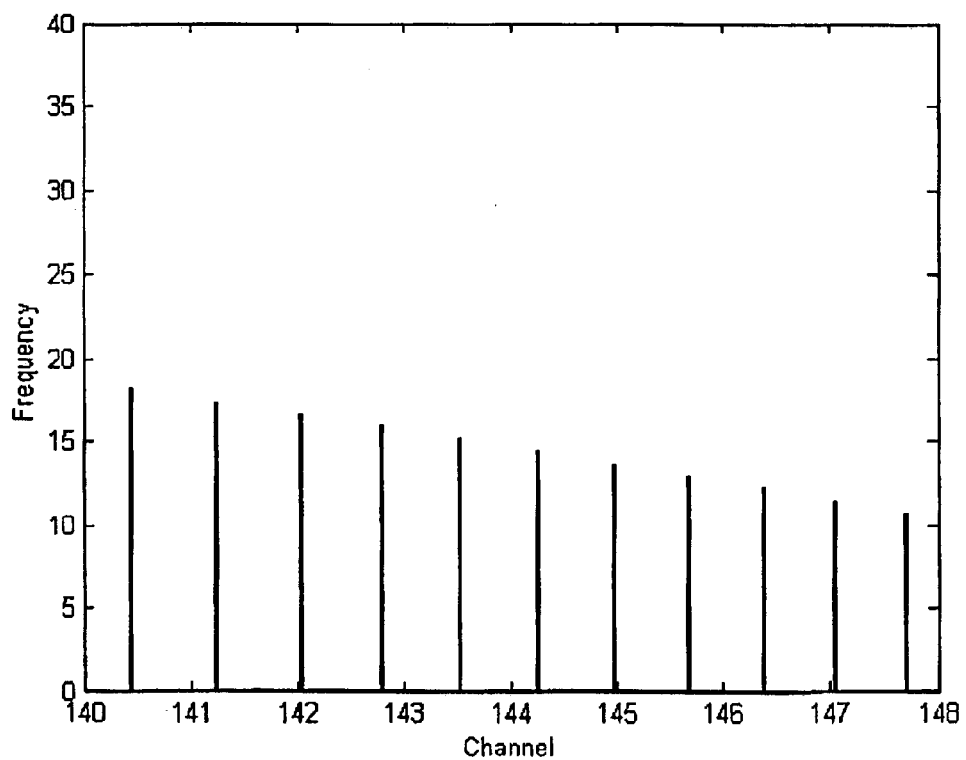
FIGS. 7(a) and 7(b) show the details of the "spikes" in the middle range channels of a log-transformed histogram.
Figure 7B:
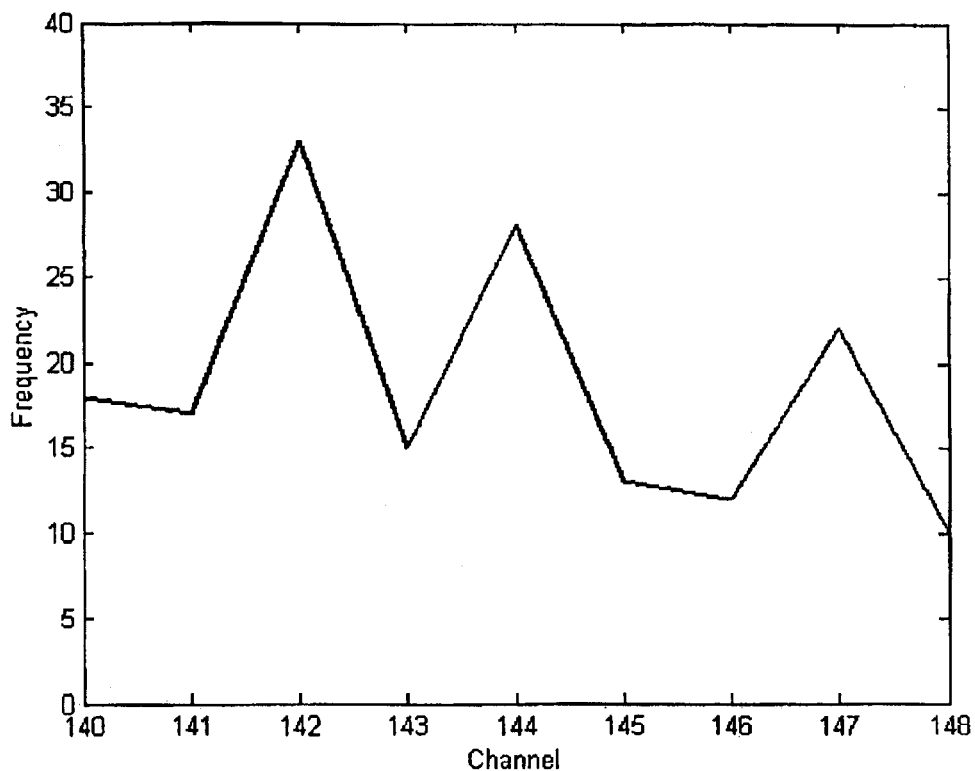
Figure 8A:
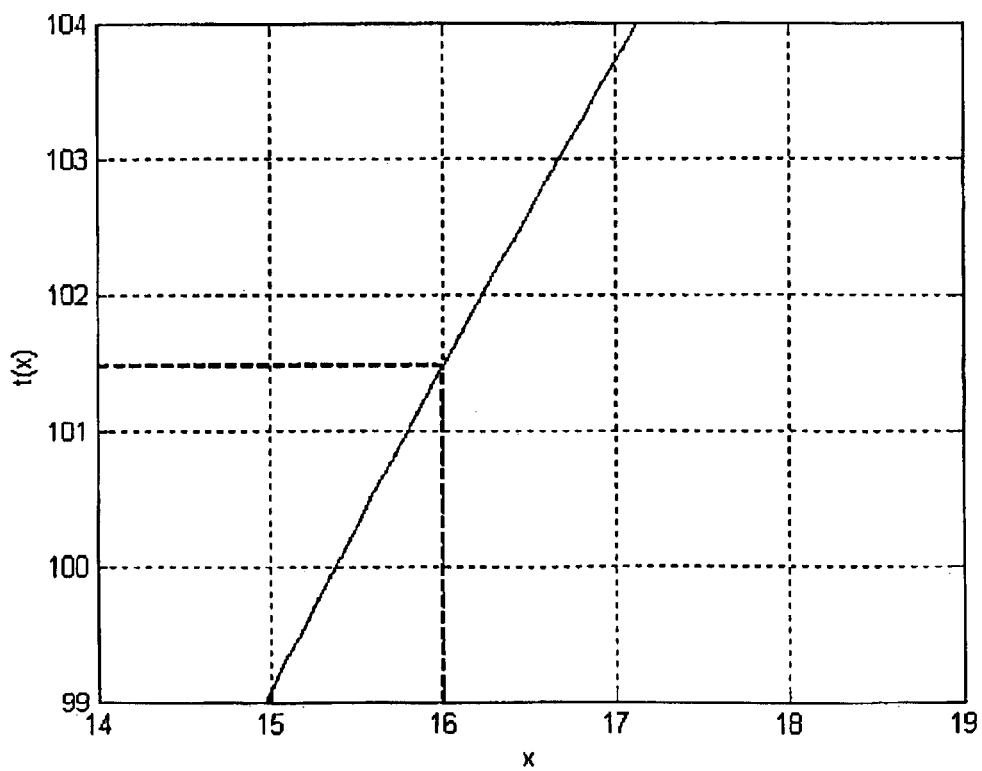
FIGS. 8(a), 8(b) and FIGS. 9(a), 9(b) depict the histogram bin contributions for low and high range channels, respectively, of a log-transformed histogram, wherein it has been assumed that the input data range [x0, x0+1] uniformly maps to the output data range [t(x0), t(x0)+1], where t(x) is the transformation (e.g., log) function.
Figure 8B:
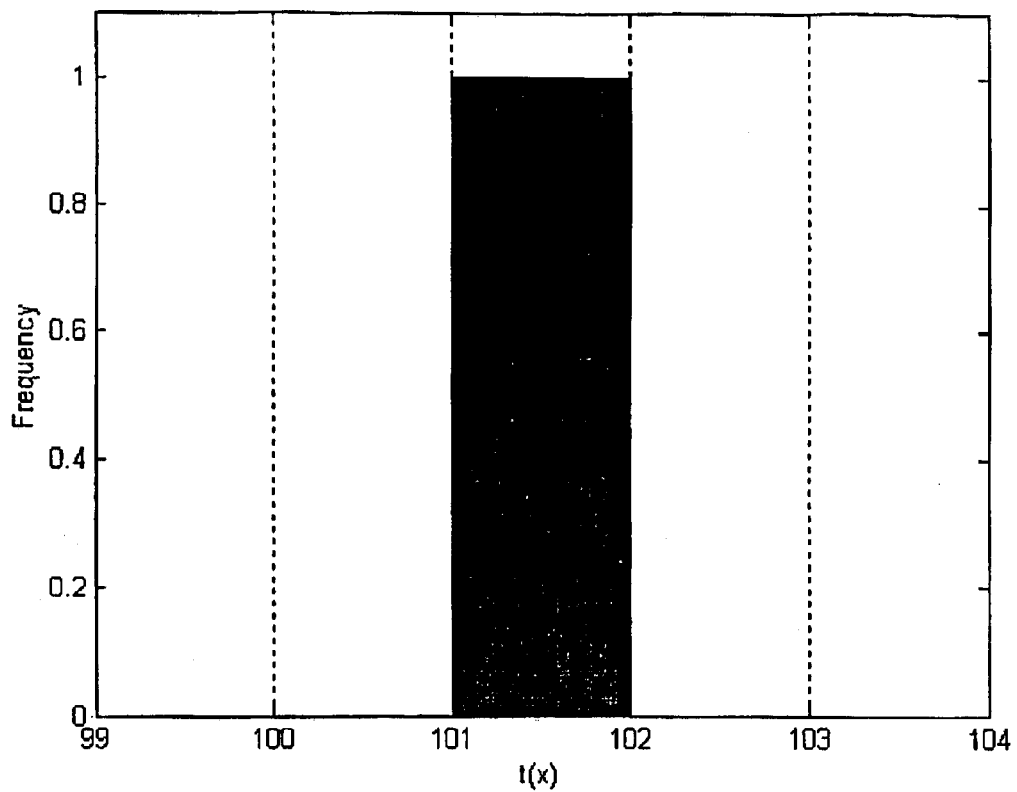
Figure 9A:
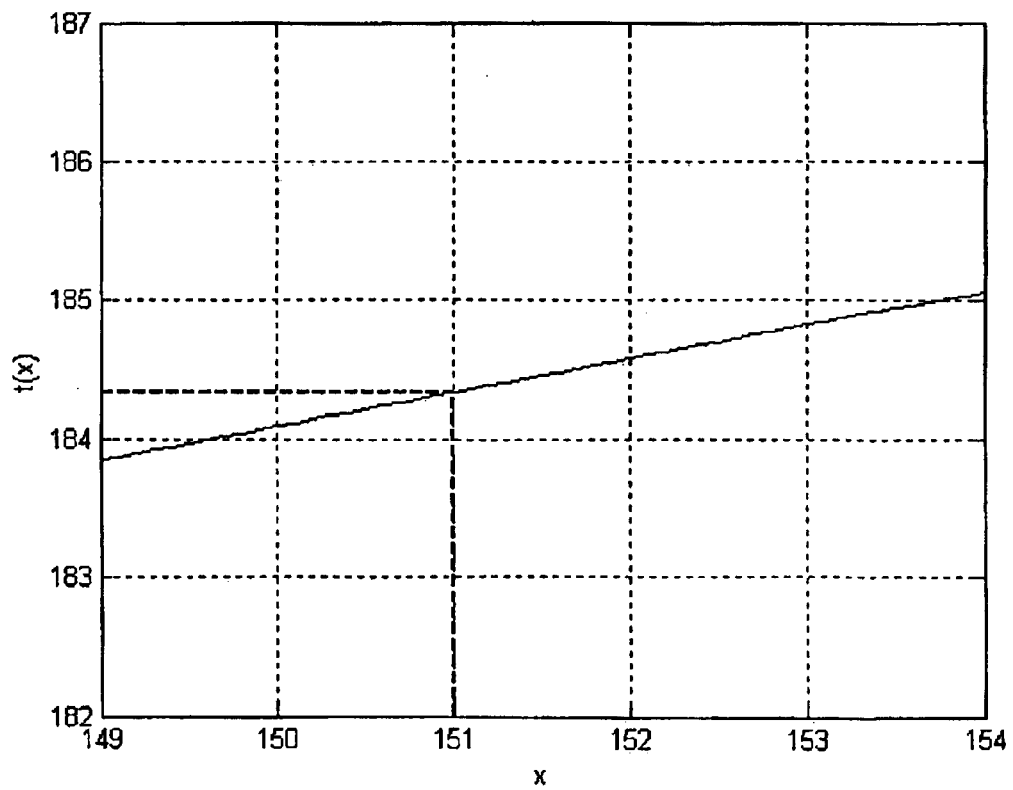
Figure 9B:
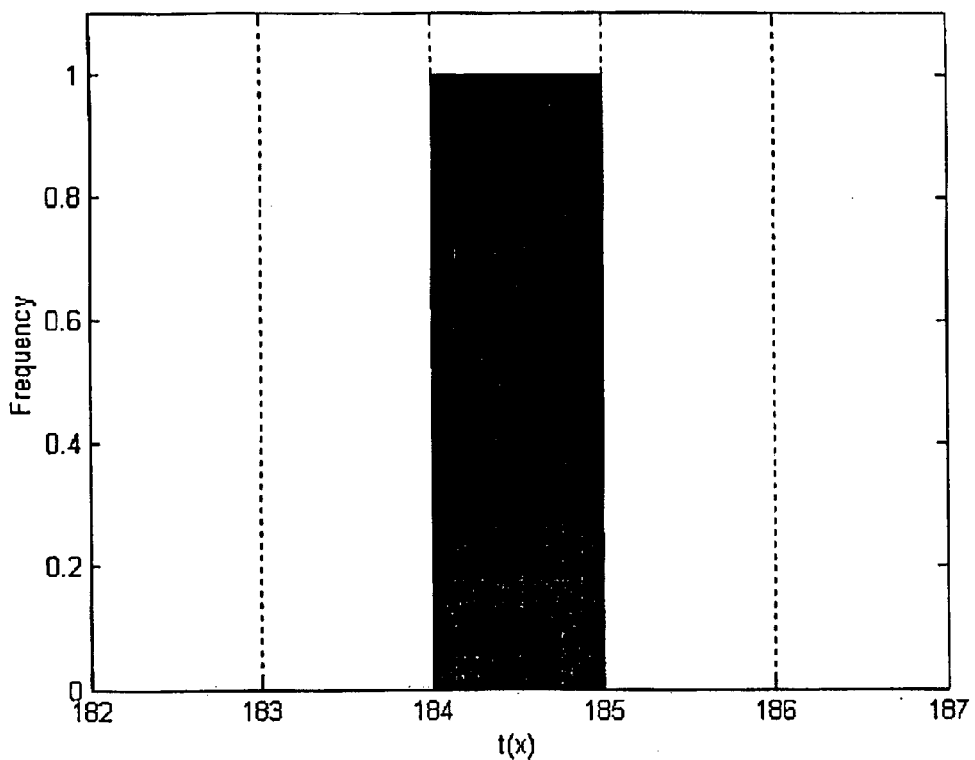

In contrast, as shown in FIG. 6(a), which illustrates mapping of middle range channels (input data range from 45 to 47 is mapped to channel 140), and FIG. 6(b) which illustrates mapping of upper range channels (input data range from 957 to 984 is mapped to channel 253, and so forth), in the middle and upper range of the histogram the logarithmic transformation actually compresses the data, so that consecutive channels may be mapped to the same channel or bin.

Where there is a change in the number of consecutive input channels that are being mapped into the same bin or channel, a "spike" is formed. The size of the "spike" will depend on the relation between the change (usually one channel) and the number of channels mapped to the bin or channel. FIGS. 7(a) and 7(b) show the details of the "spikes" in middle range channels. In this range the number of consecutive input channels being mapped into the same bin changes from one to two, and back to one again. Therefore, the "spikes" double the amplitude and are very noticeable. In the high range histogram channels the change could be one channel over 20 to 30 channels mapped into the same bin, generating small "spikes".

As a result of their analysis of the transform mechanism and the data upon which it operates, to be discussed below, the present inventors have concluded that the binning effect is produced as a result of the inconsistent premise that the input range [x0, x0+1) will uniformly map to the output range [t(x0), t(x0)+1), where t(x) is the transformation (e.g., log) function. In other words, it has been conventional wisdom that the contribution of an input data value x0 is one unit in the output histogram bin t(x0).

FIGS. 8(a), 8(b) and FIGS. 9(a), 9(b) depict respective bin contributions for low and high range channels, under this inconsistent assumption. As shown therein, although the input values are in ranges where the transformation expands and compresses the data, the bin contribution to the output histogram is assumed to be the same.

To correctly map the input data from the ADC converter to the transformed domain, the converter's digitization process needs to be closely examined. In mathematical terms, the digitization process of an analog-to-digital converter implements a "floor" function. This means that for the analog data range [x0, x0+1), the output will be the integer digital value x0. Without a loss in generality, a one-to-one correspondence between the analog input metric units and the digital output of the ADC converter may be assumed. If the probability distribution of the input data sample in the range [x0, x0+1) is known, then it is possible to determine the probability distribution in the transformed domain.

When the input data is transformed from the input domain, X, to the output domain, Y, using a given transformation Y=t(X), the input probability distribution, $f_X(x)$, is transformed into $f_Y(y)$. Because the transformation does not affect the probability of each event, the infinitesimal probability of any point x is the same at the output value y=t(x). In mathematical terms this is expressed in Equation (2) as follows:

$$f_Y(y)*dy=f_X(x)*dx \qquad (2)$$

By a simple manipulation and substituting x by $t^{-1}(y)$, the relationship between the resulting probability distribution, $f_Y(y)$, and the input probability distribution, $f_X(x)$, is given in Equation (3) as:

$$f_Y(Y)=f_X(t^{-1}(y))*d/dy(t^{-1}(y)) \qquad (3)$$

where X and Y are two random variables related by the transformation Y=t(x), and t(x) is a monotonically increasing transformation function whose inverse $t^{-1}(y)$ has a continuous derivative on Y. Equation (2) also guarantees that the areas under the input and output probability distributions are maintained, which is an important requisite when analyzing cell populations.

For the particular case of the generic log transformation of Equation (1) above, the transformed density distribution is given in Equation (4) as:

$$g(y)=f(K*e^{y/S})*K*S*e^{y/S} \qquad (4)$$

where S and K are scaling constants defined as $S=D/(B-1)$ and $K=2^R/10^D$, B is the number of bins in the output histogram, D is the number of desired decades, and R is the bit resolution of the ADC converter.

In order to employ Equation (4), it is necessary to know the probability distribution of the input histogram, which is unknown but can be approximated, as will be described. As suggested above, the binning effect may be thought as the result of assuming that the input probability distribution at each ADC interval is a delta function positioned at each ADC output value. In actuality, however, this erroneous assumption is the least probable case when dealing with biological events, such as biological cell populations.

Figure 1B:
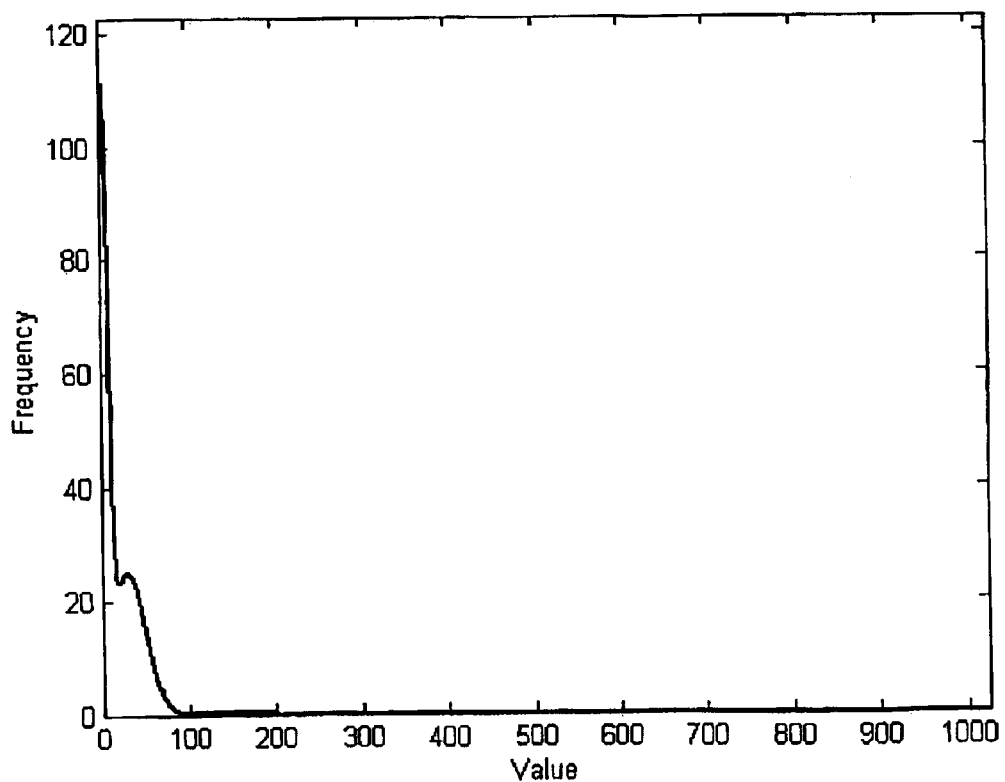
Figure 1C:
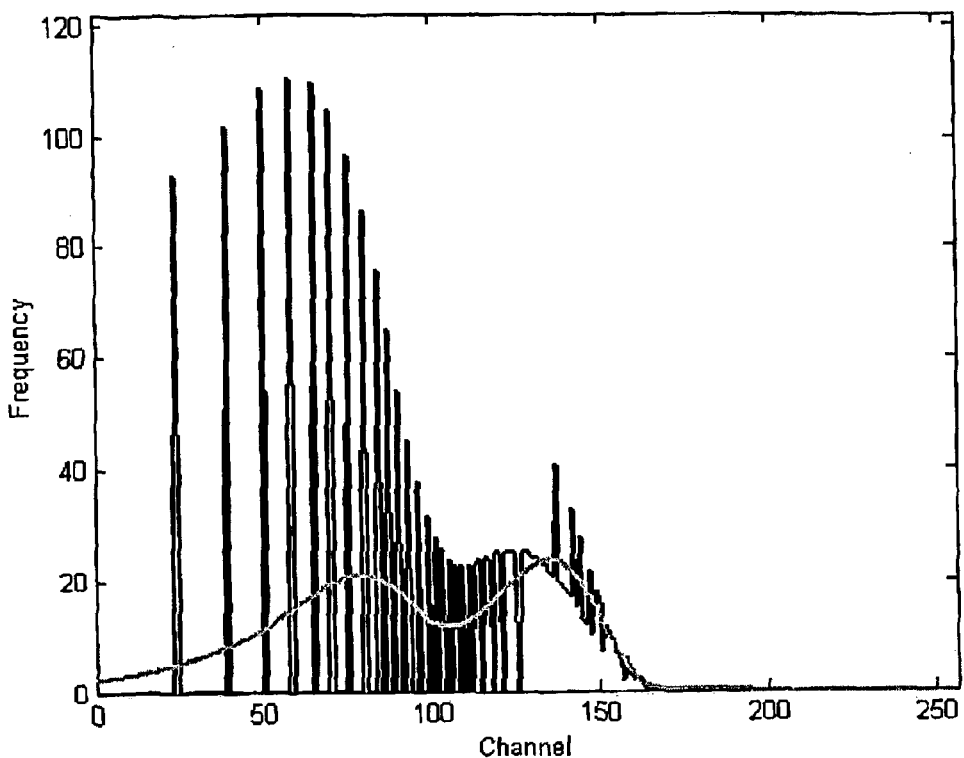
Figure 2A:
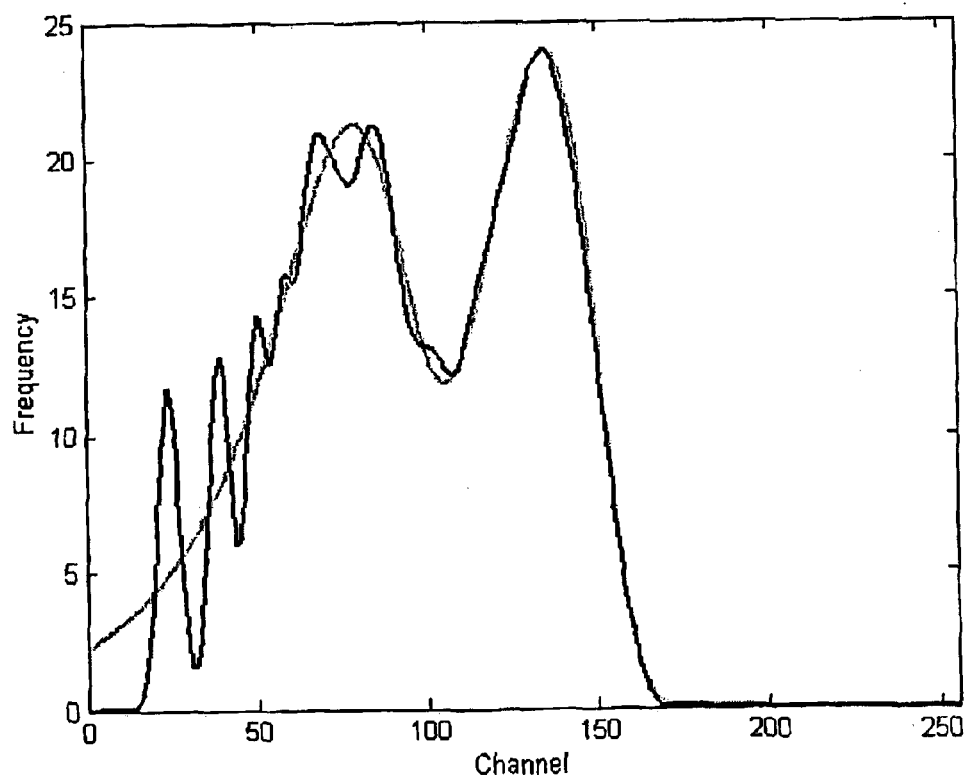
FIGS. 2(a), 2(b), 2(c) and 2(d) respectively illustrate the effects of an FIR filtering scheme, after 20, 100, 200 and 500 passes of the binned histogram of FIG. 1(c) through an FIR filter.
Figure 2:
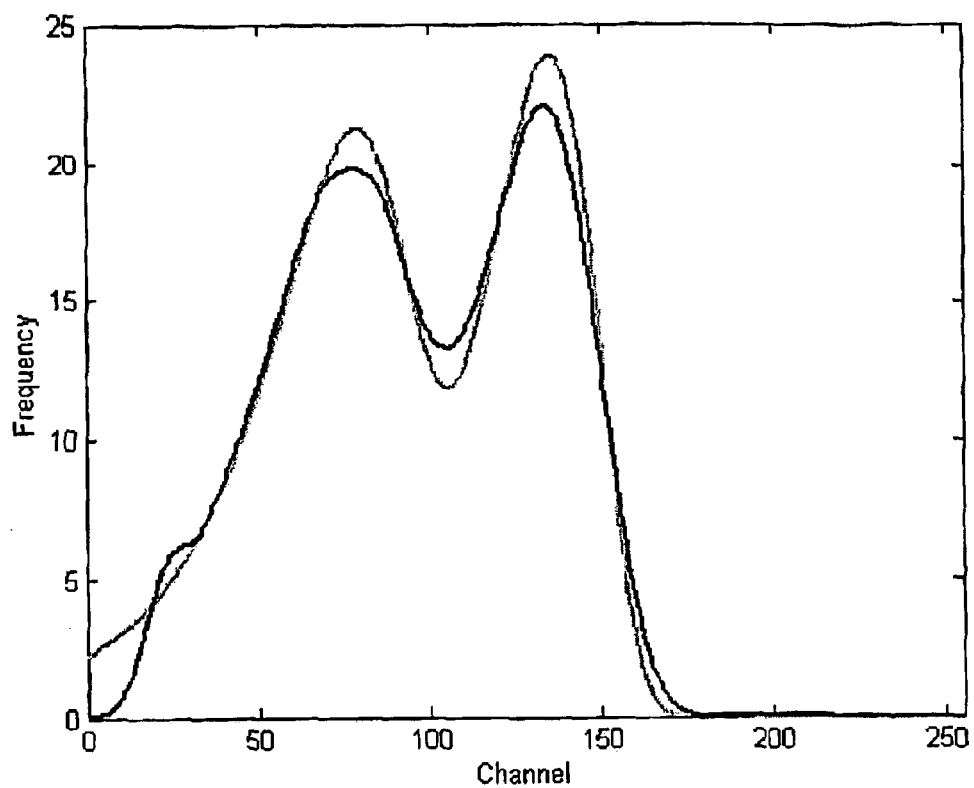
Figure 2:
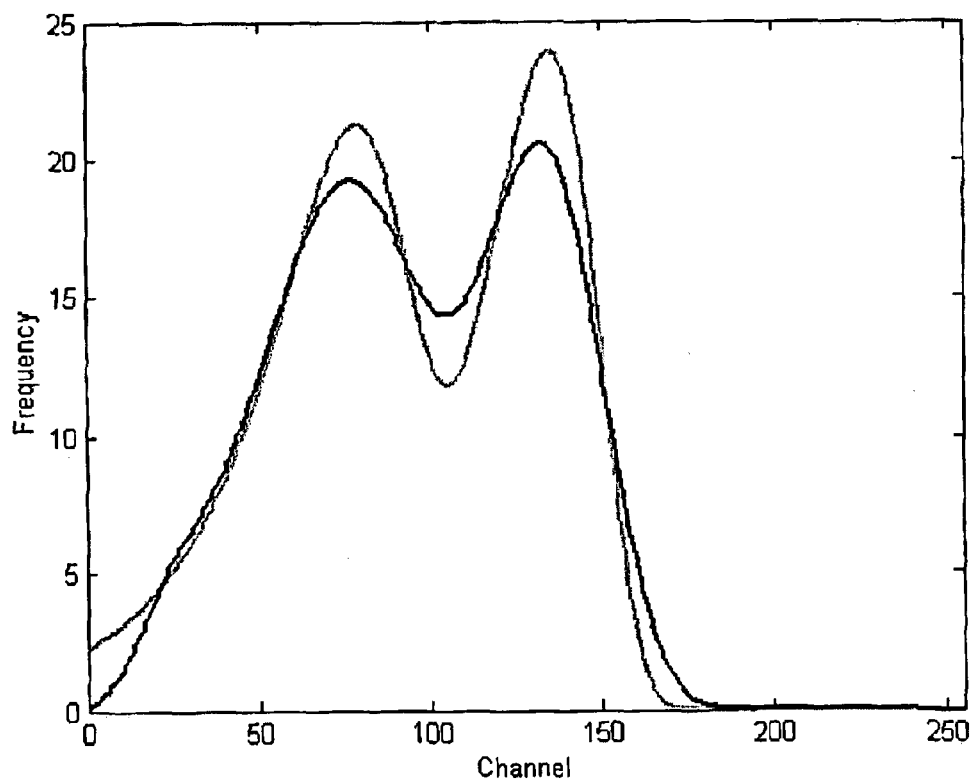
Figure 2:
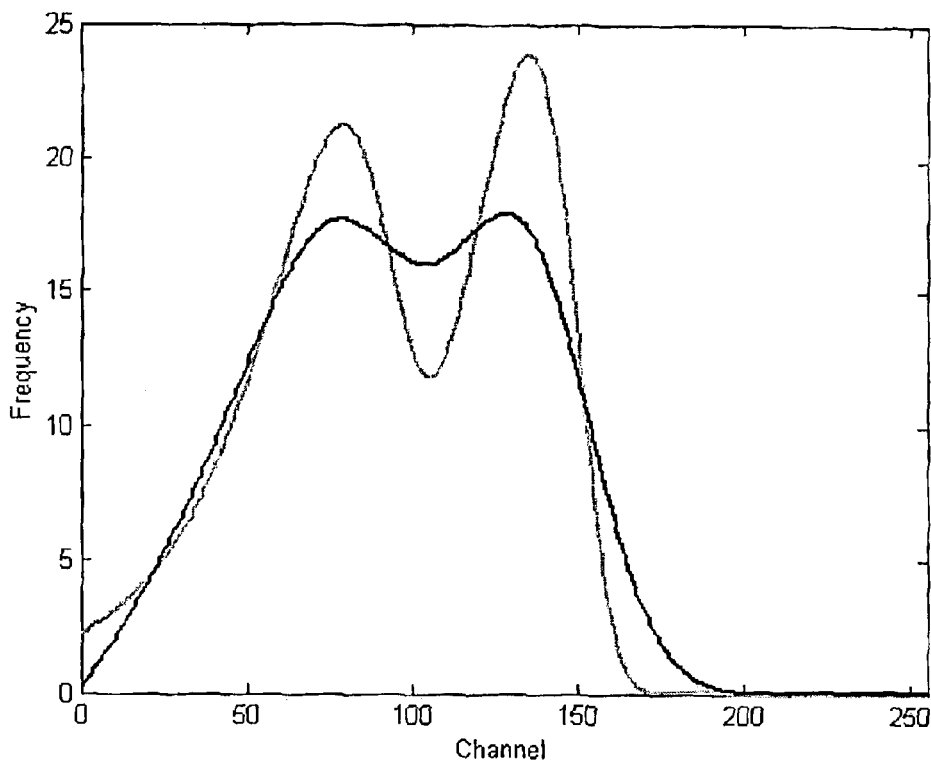
Figure 10A:
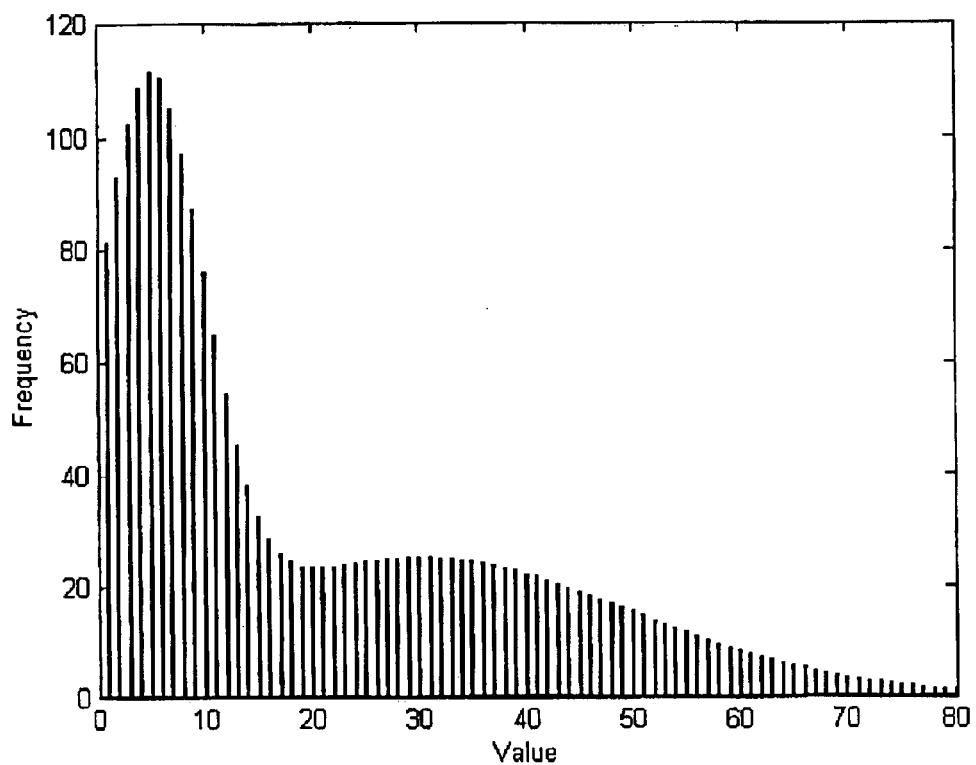
FIG. 10(a) shows the delta approximation for the input histogram of FIG. 1(b)
Figure 10B:
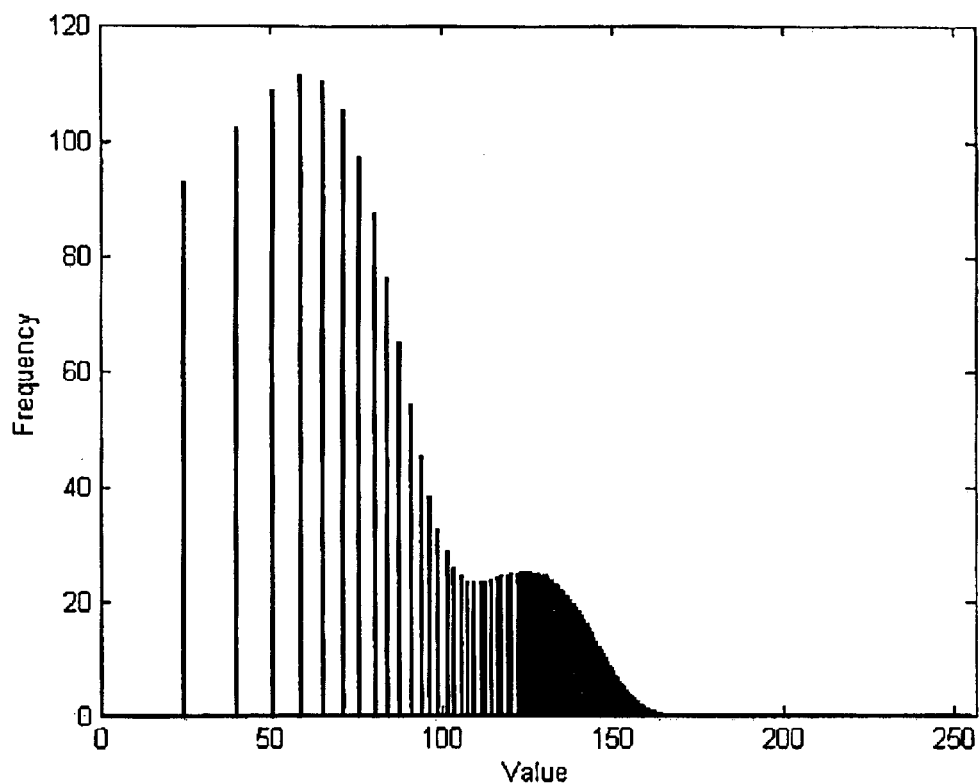
FIG. 10(b) shows the results of transforming input data using Equation (4)
Figure 10C:
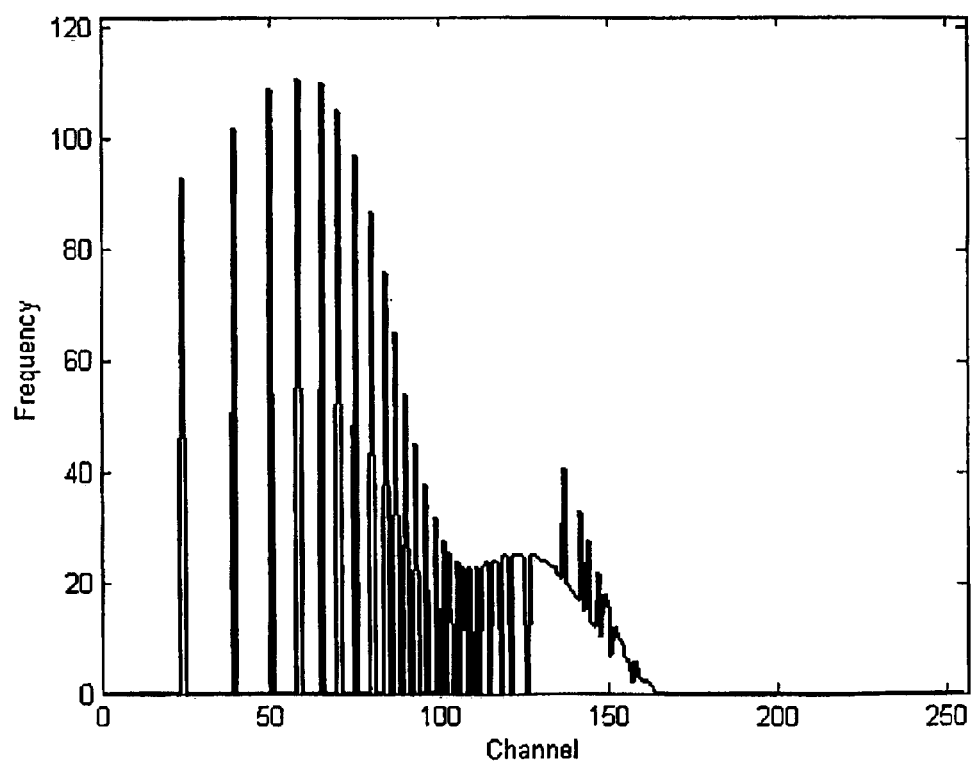
FIG. 10(c) shows the accumulation in an output histogram of the transformed data.

FIG. 10(a) shows the delta approximation for the input histogram of FIG. 1(b), FIG. 10(b) shows the results of transforming the input data using Equation (4), and FIG. 10(c) shows the accumulation in an output histogram of the transformed data.

The use of a more realistic probability distribution at each ADC interval will provide a better log-transformation. This may involve the use of a uniform approximation, a linear approximation, and any upper order approximation. The effect of each is described below.

Uniform Approximation

Figure 11A:
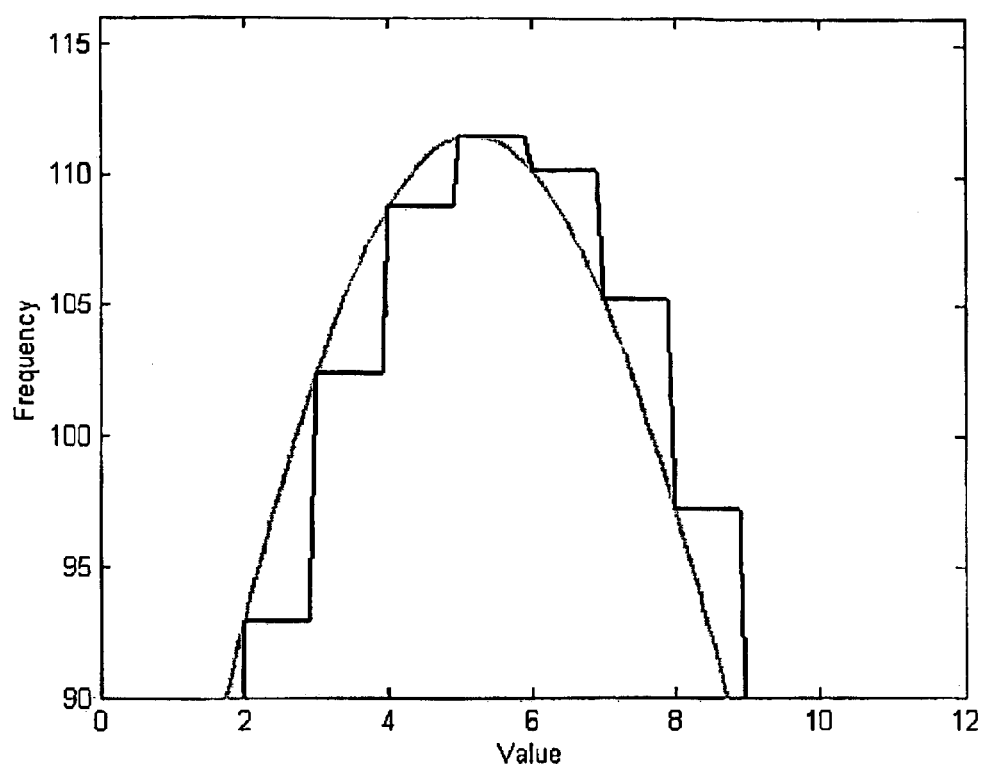
FIG. 11(a) shows a lower range portion of the input data distribution of FIG. 1(b) assuming a uniform distribution at each ADC interval.
Figure 11B:
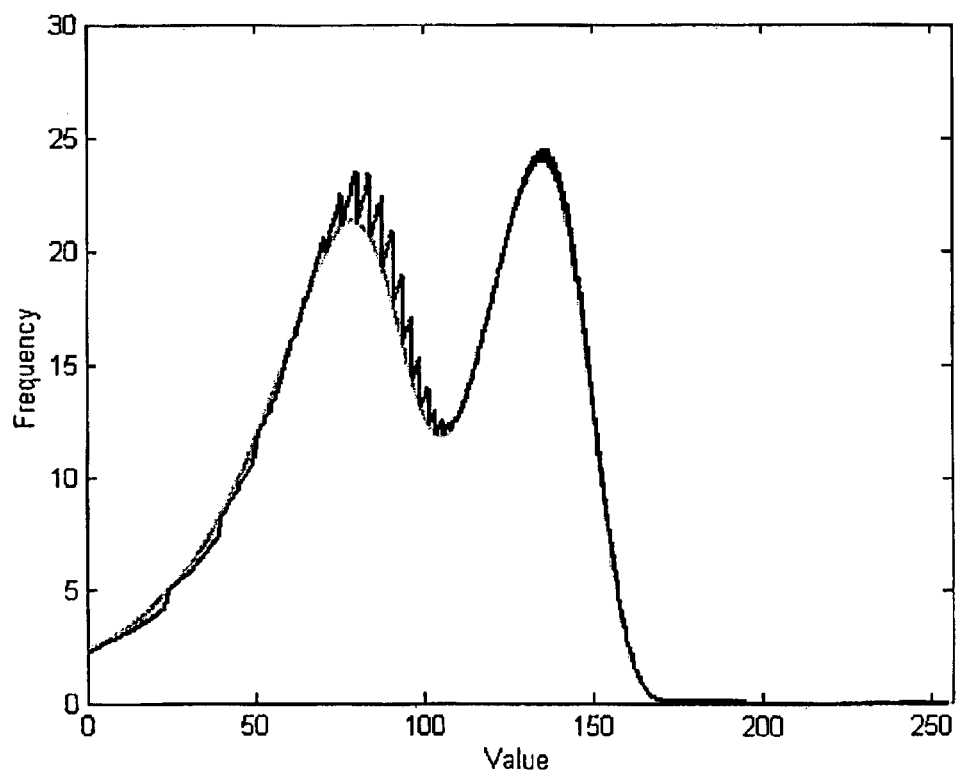
FIG. 11(b) shows the log-transformation of a histogram using uniform approximation to achieve statistical probability distribution-preservation.

The simplest approximation, and far better than the original delta approximation, described above, is the uniform approximation. In this case, the probability distribution of the input data in each ADC step is assumed to be uniform. FIG. 11(a) shows a lower range portion of the input data distribution of FIG. 1(b) assuming a uniform distribution at each ADC step. When this input data is log-transformed using the probability of Equation (4), the resulting histogram more closely resembles the ideal transformation as shown in FIG. 11(b). In this case, both major binning effect artifacts are substantially reduced, since the input domain is now assumed continuous. In addition, although is not an ideal transformation, the area under the curve is maintained. As described below, the uniform approximation can be implemented in real-time by using look-up tables.

Although the uniform approximation provides results similar to the ideal transformation, these results are not perfect. Such imperfections are more visible in the lower range at the locations of the "holes" of the binned histogram. These imperfections are the direct result of the difference between the actual input distribution and the uniform approximation made.

Figure 12:
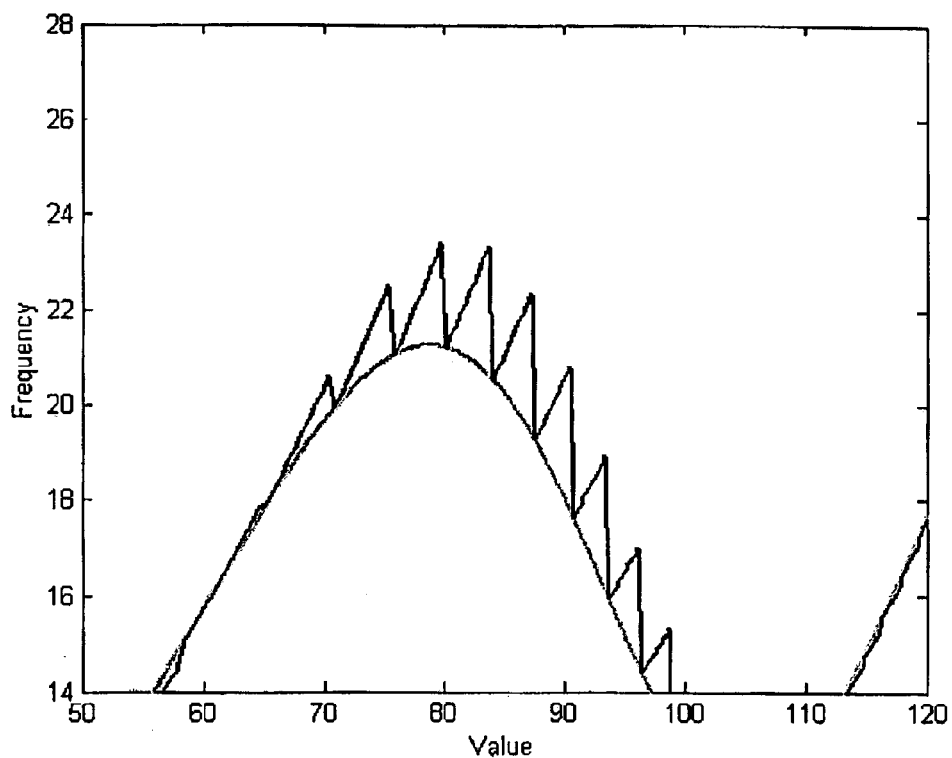
FIG. 12 shows imperfections in a corrected histogram transform where the actual input distribution differs substantially from the uniform approximation.

FIG. 12 shows the details of the imperfections where the actual input distribution differs substantially from the uniform approximation. To improve upon the results obtained with the uniform approximation it is necessary to employ a higher order approximation, such as a linear approximation, described below.

Linear Approximation

Figure 13A:
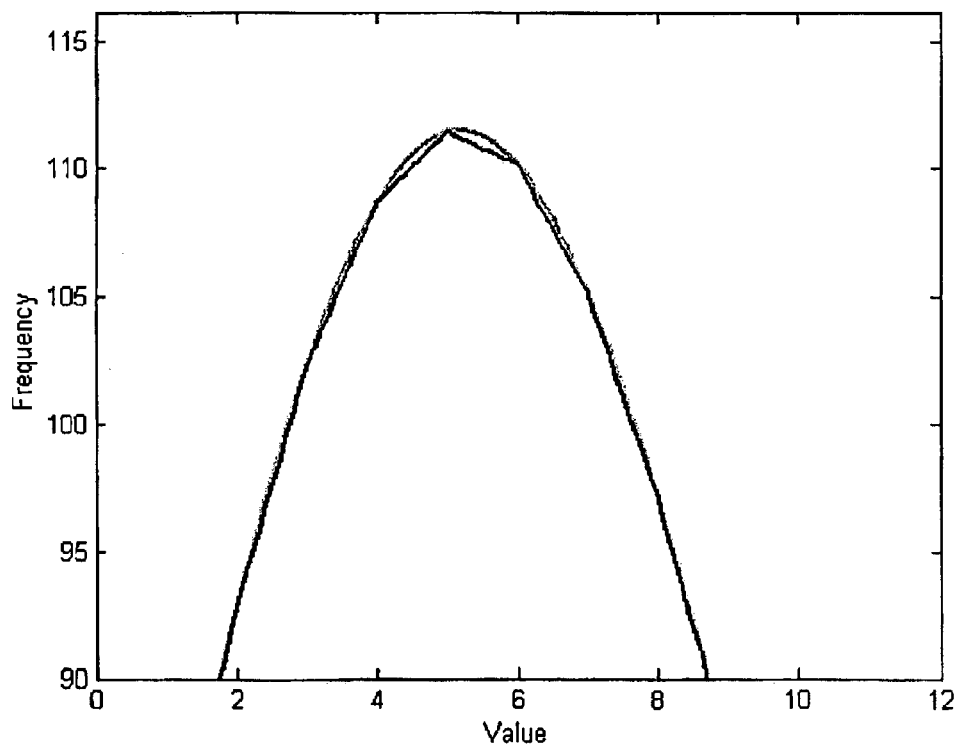
FIG. 13(a) shows a lower range portion of the input data distribution of FIG. 1(b) assuming a linear distribution at each ADC interval.
Figure 13B:
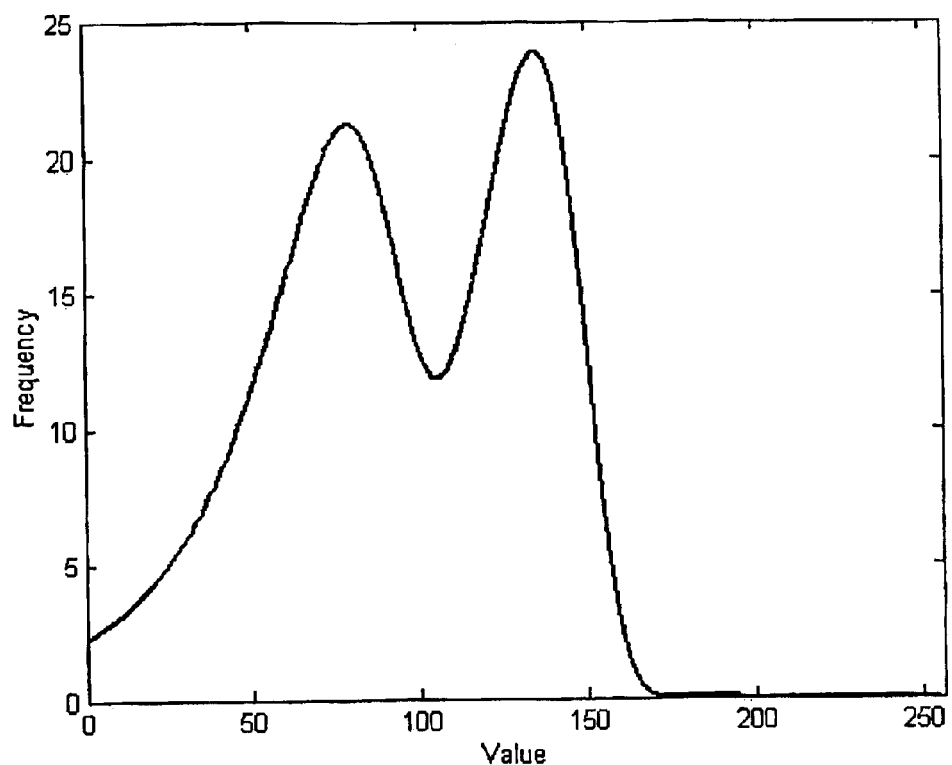
FIG. 13(b) shows the results of using Equation (4) under the assumption that the input data distribution is linear at each ADC interval.

After the uniform approximation, the next increasingly complex approximation that can be used is the linear approximation. In this approximation, the probability distribution of the input data in each ADC step is assumed to be linear. FIG. 13(a) shows a lower range portion of the input data distribution of FIG. 1(b) assuming a linear distribution at each ADC step. FIG. 13(b) shows the results of using Equation (4) under the assumption that the input data distribution is linear at each ADC interval. In this case, the results are practically identical to the ideal log-transformation, shown in the gray curves of FIGS. 2(a)–2(d), referenced above. As in the case of uniform approximation, the area under the curve is also maintained.

Now even though the results can be improved using higher approximations, such as polynomial approximations, it does not make practical sense to do so, because the natural variability of biological populations is likely to be far greater than the error of the approximation made. It is important to note that the amplitudes of the output histogram are non-integer; therefore, it is impossible to create a sequence of data points that can generate the same histogram. This fact makes it impossible to directly enumerate, on an event by event basis, cell populations based on the analysis results of the output histogram; however, this drawback is easily overcome by performing an inverse transformation of the analysis results into the input domain and enumerating the cell populations using the input events.

Figure 14A:
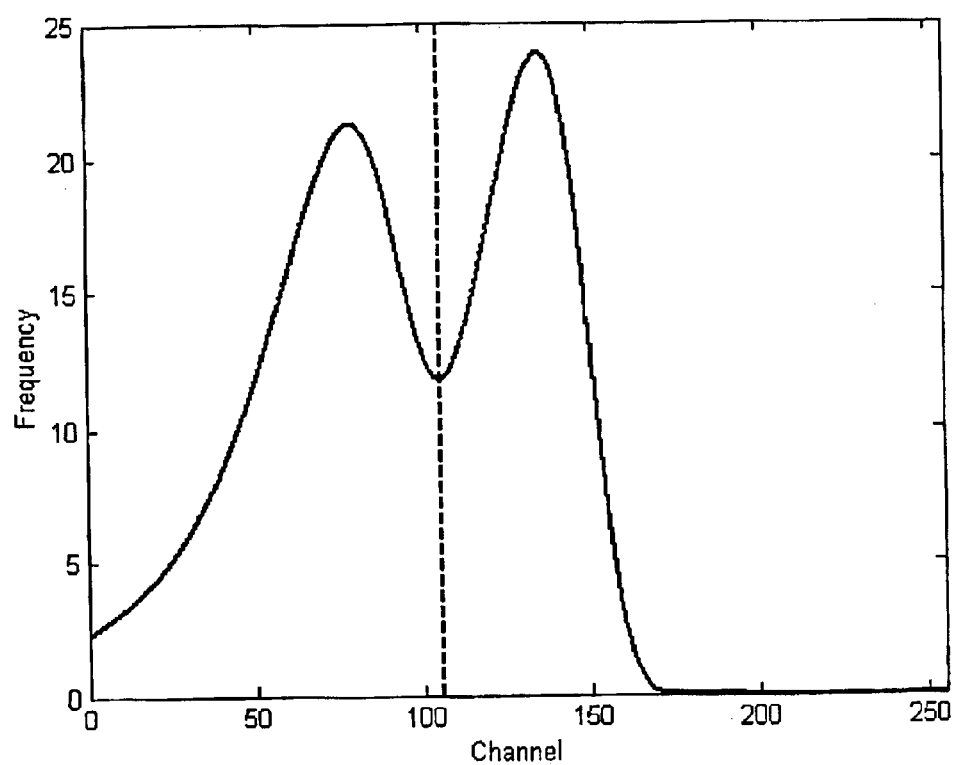
FIG. 14(a) shows a valley in a log-transformed histogram.
Figure 14B:
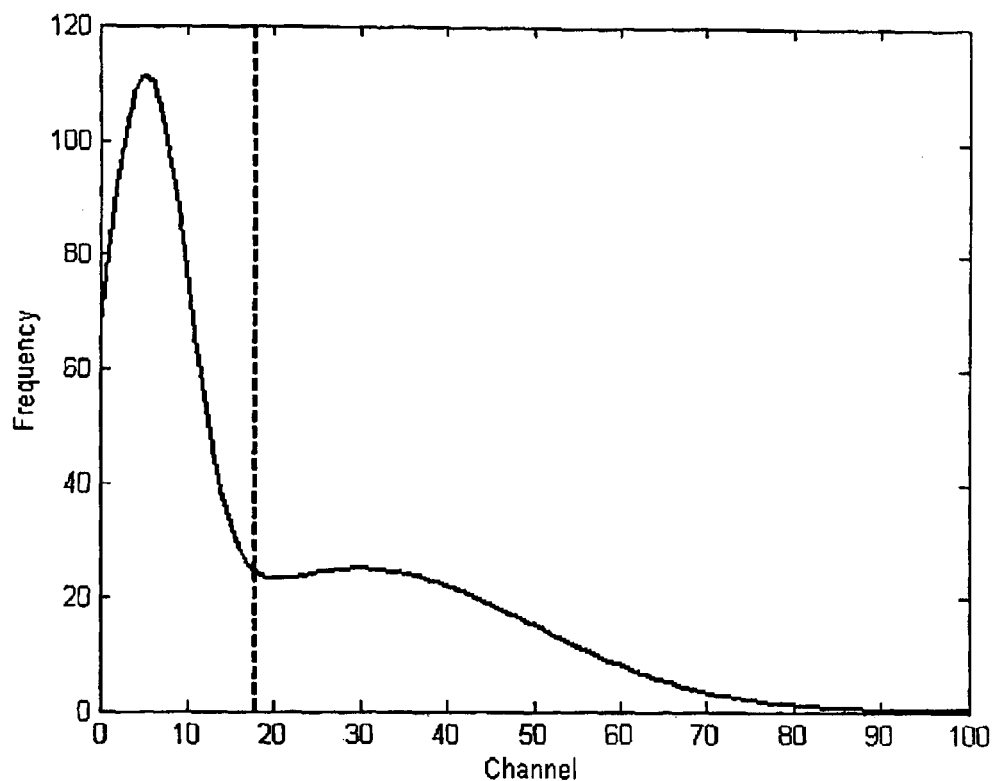
FIG. 14(b) shows a valley mapped to the input domain of a histogram.

FIGS. 14(a) and 14(b) graphically illustrate how the valley, demarcated by a vertical broken line, obtained by processing the output histogram can be mapped to the input domain and used to enumerate the cell populations. In particular, FIG. 14(a) shows the valley in the output histogram, while FIG. 14(b) shows the valley mapped to the input domain.

From the foregoing description, it will be readily appreciated that the problem of binning artifacts encountered in conventional log-transformation operations performed on digitized data can be effectively eliminated by new and quasi-optimal methodology to accumulating logarithmically transformed data into integer histograms, that operates to preserve the probability distribution of the data. With this new approach to data mapping, the need for filtering becomes a non-issue, since the binning effect is countered early in the process, thus preserving the statistical properties of the populations under study.

In order to employ the signal processing operator of the invention in flow cytometer instrumentation, it is preferable to implement it in real-time. In this context, the term 'real-time' means the ability to process each data point as it is being acquired, or to process all of the data after acquisition substantially instantaneously (e.g., within an interval of less than 200 milliseconds). In order to achieve real-time performance it is necessary to consider the contribution to the output histogram for each acquired data point. The following discussion presents a mechanism for accumulating a data point as it is being acquired in the resulting log-transformed histogram.

In order to process input data points in real-time it is necessary to process them one-by-one, and the objective is to accumulate the histogram as the data points are being acquired. As described earlier, it is impossible to generate a data sequence that can be accumulated to generate the desired log-transformed histogram. Therefore, it is necessary to develop a new histogram accumulation technique, which is capable of building the desired histogram as the input data points are gathered.

Using Equation (4) and assuming that the probability distribution for any given input data range [x0, x0+1) is uniform, then a non-integer bin or channel contribution in the output histogram can be computed by applying Equation (4) to each input data point. The bin/channel contributions are then accumulated to form the output histogram.

FIGS. 15(a), 15(b) and FIGS. 16(a), 16(b) show the non-integer bin contributions for a low and a high range channel, respectively, using this new method.

Figure 15A:
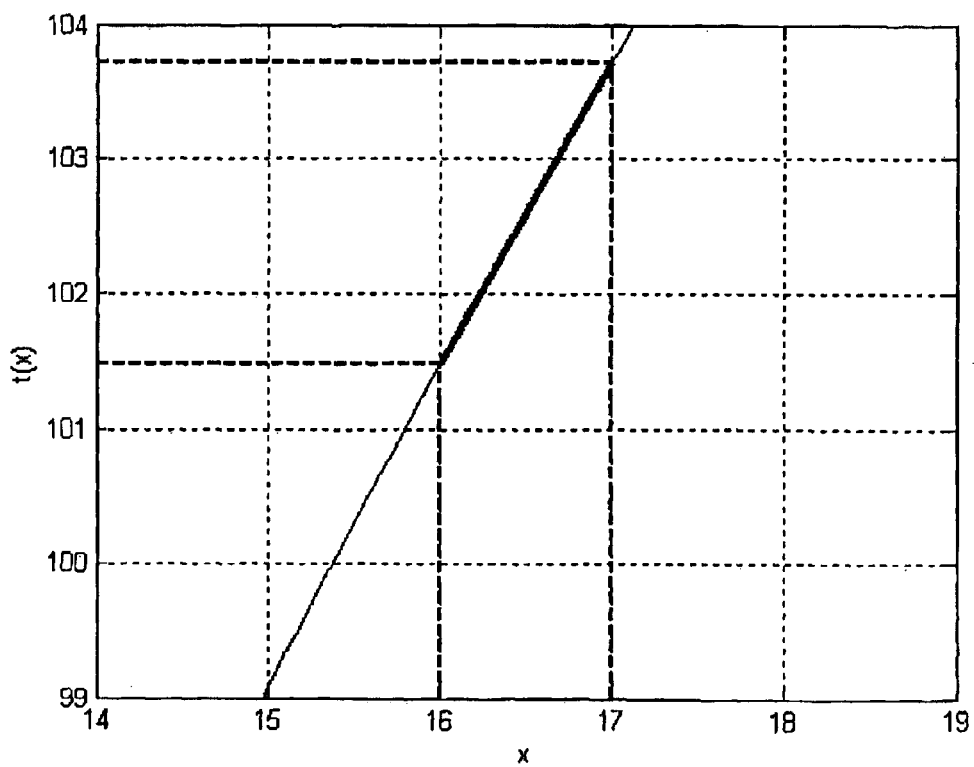
FIG. 15(a) graphically depicts how a histogram input range [16, 17) maps to transformed histogram output channels between 101 to 103.
Figure 15B:
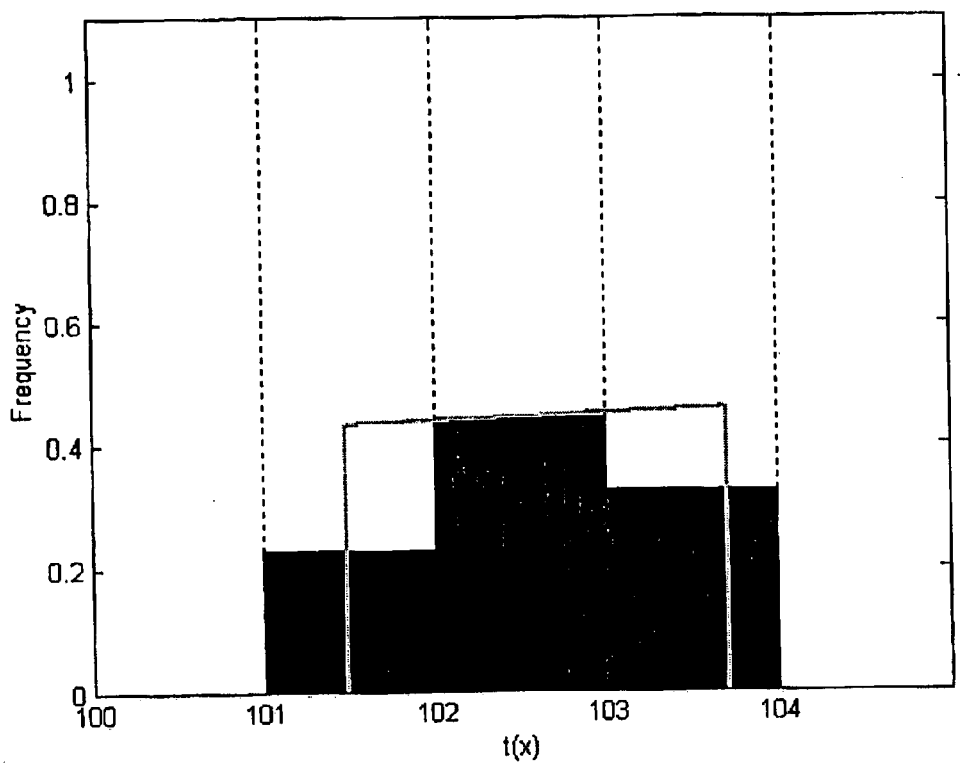
FIG. 15(b) shows an exact histogram transformation using Equation (4), for a uniform unit distribution in the data range [16, 17)

In particular, FIG. 15(a) graphically depicts how the input range [16, 17) maps to output channels between 101 to 103. The gray curve in FIG. 15(b) represents the exact transformation using Equation (4), for the uniform unit distribution in the range [16, 17). The area under the gray curve has a value of one, as expected. Because the output histogram bins have integer boundaries, the area under the gray curve in each bin is computed and assigned to that bin. In FIG. 15(b), the resulting non-integer bins are shown in black, with the total area of the bin contributions summing to a value of one.

The next data range [17, 18) generates an overlapping contribution starting from channel 103, causing a "filling-in" of the area not covered by the upper part of the range [16, 17) interval. This "spreading" of one input data point into several non-integer bins and the overlapping contributions between contiguous input data points is what fills the discontinuities or "holes" and eliminates the "spikes" observed in the typical binned histogram of FIG. 3.

Figure 16A:
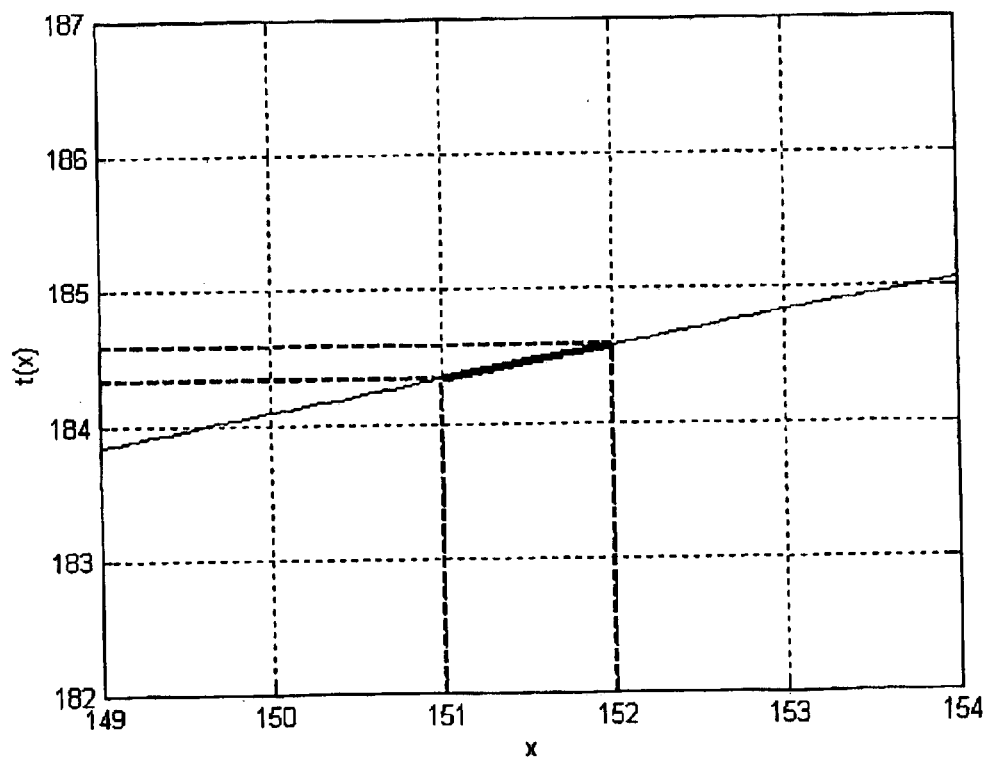
FIG. 16(a) shows how a histogram input range [151, 152) maps to transformed histogram output channel 184.
Figure 16B:
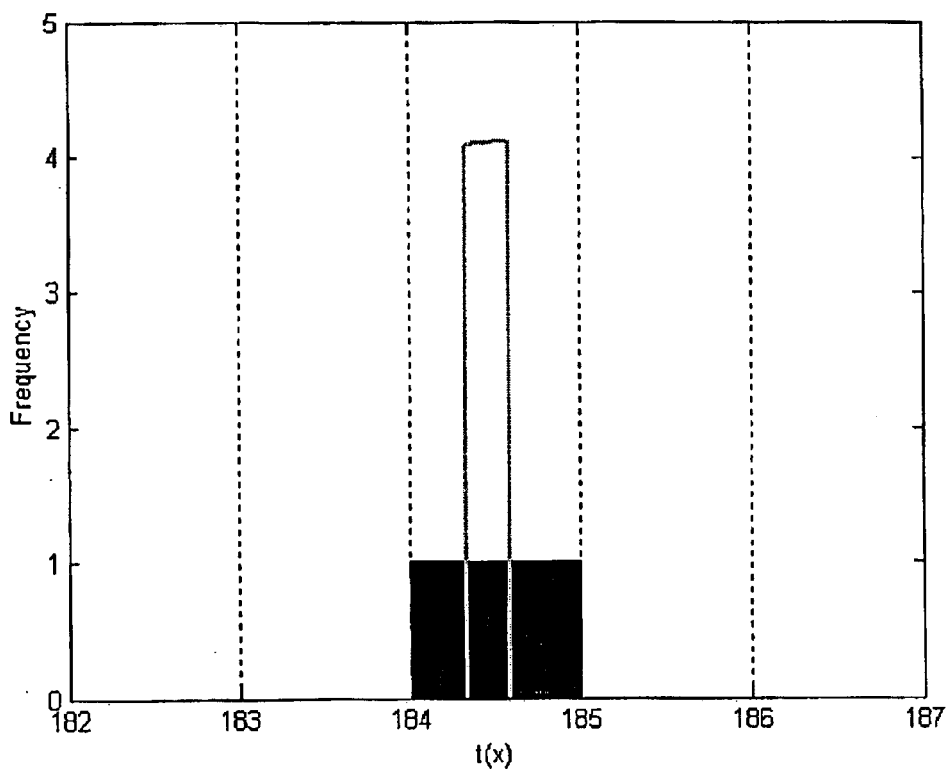
FIG. 16(b) shows an exact transformation using Equation (4), for a uniform unit distribution in the data range [151, 152)

On the other hand, FIG. 16(a) shows how the input range [151, 152) maps to the output channel 184. The gray curve in FIG. 16(b) represents the exact transformation, using Equation (4), for the uniform unit distribution in the range [151, 152). In this case, since the input range maps inside a single bin, the resulting bin in the output histogram will have a unit area regardless of the shape of the probability distribution in the [151,152) interval, as shown in FIG. 16(b).

Figure 17A:
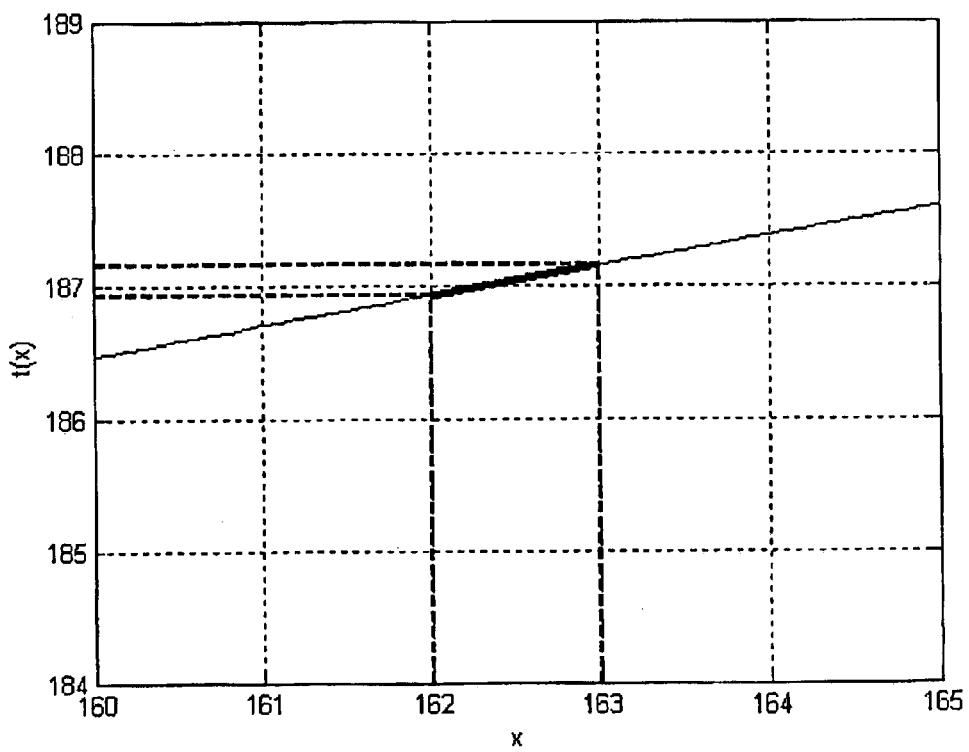
FIG. 17(a) shows how a histogram input data range [162, 163) maps to transformed output channels 187 and 188.
Figure 17B:
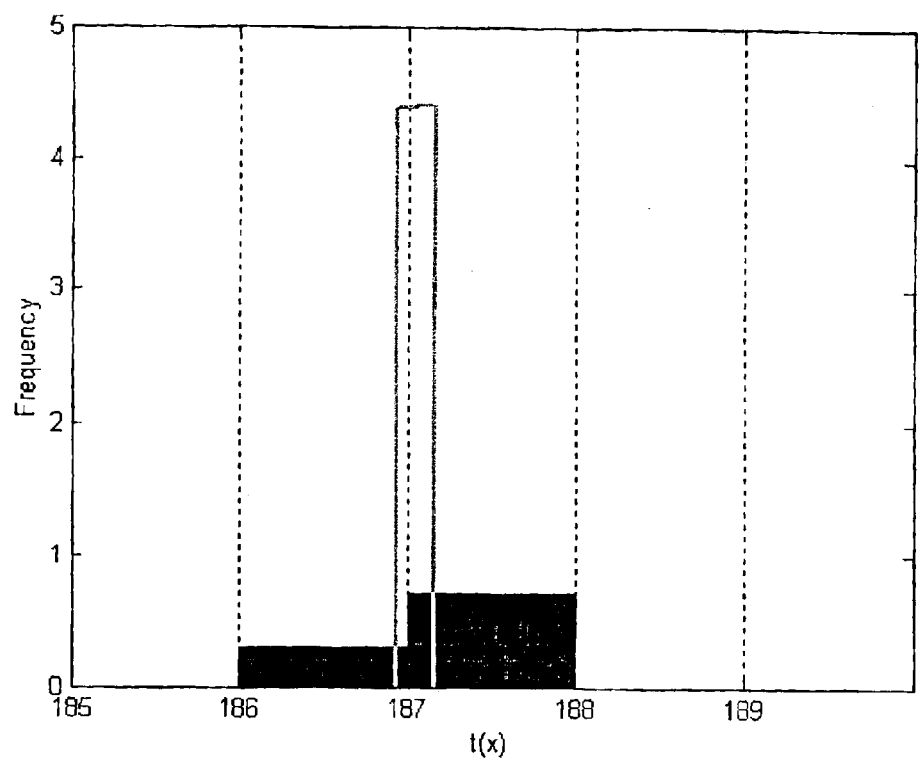
FIG. 17(b) shows an exact transformation using Equation (4), for a uniform unit distribution in the data range [161, 162)

FIG. 17(a) shows how the input range [162, 163) maps to the output channels 187 and 188. The gray curve in FIG. 17(b) represents the exact transformation, using Equation (4), for the uniform unit distribution in the range [162, 163). In this case, even though the input range maps to a range smaller than a single bin, this resulting contribution falls in the boundary of the bins 187 and 188, generating a non-integer bin contribution that spreads into two bins.

These different types of non-integer bin contributions for the log transformation are computed and accumulated for each point that needs to be mapped from the original domain to the transformed domain. Each set of bin contributions is different and is a function of the position of the histogram channel. This technique may be readily implemented using look-up tables.

More particularly, a relatively fast way to accumulate the histogram is to have pre-computed in memory all necessary non-integer bin contributions indexed by input channel. These pre-computed values can then be used as a look-up table to provide fast access to the information. The non-integer contributions must be described in such a way to allow for efficient retrieval from memory and adding them to the output histogram.

One way to describe a non-integer contribution is to use an initial Bin, a final Bin, and the area of each non-integer bin contribution. Given the previous structure, the following pseudo-code describes a the procedure to accumulate each input data point as it is being acquired:

For each input data point:
1. Retrieve the non-integer contribution from the lookup table.
2. For each area in the non-integer contribution, add the area at the appropriate bin in the output histogram.

To generate the look-up table in memory it is necessary to compute each non-integer contribution parameter described earlier. The initial bin, $Bin_{ini}$, is the first integer bin position that is smaller than or equal to the transformed input value x:

$$Bin_{ini}(x) = \text{floor}(t(x)) \quad (5)$$

The final bin, $Bin_{end}$, is the first integer bin position that is greater than or equal to the transformed input value x+1:

$$Bin_{end}(x) = \text{ceil}(t(x+1)) \quad (6)$$

The center bins are all the bins between the initial and final bins.

The last step is to compute the areas associated to each bin. FIG. 15(b), described above, depicts an example of how a unit input at a channel is mapped to its non-integer contribution.

To compute each non-integer contribution area it is necessary to integrate Equation (3) inside each integer bin range. Given a function A(y) that defines the integral from 0 to y, the area inside each bin can be computed as the difference of A(y) evaluated at the boundaries inside each bin.

The following Equation (7) shows the mathematical expression of A(y) in terms of the input probability distribution, $f_X(x)$, and the inverse transformation function, $t^{-1}(y)$:

$$A(y) = \int_0^y f_X(t^{-1}(y)) * \frac{d}{dy} t^{-1}(y) \quad (7)$$

Since $f_X(x) = 1$ when a uniform distribution is assumed, Equation (7) can be simplified as shown in Equations (8) and (9):

$$A(y) = \int_0^y \frac{d}{dy} t^{-1}(y) \quad (8)$$

$$A(y) = t^{-1}(y) \quad (9)$$

The calculation of the bin area can be divided into three cases: 1- the initial area, $A_{ini}$; 2- the center bins area, $A_{center}$; and 3- the final area, $A_{end}$. The initial area, $A_{ini}$, is the area between the end of the initial bin, $Bin_{ini}+1$, and the transformed data point x, as shown in Equation (10):

$$A_{ini} = A(Bin_{ini}+1) - A(t(x)) = A(Bin_{ini}+1) - x \quad (10)$$

The center bins area, $A_{center}$, is the area between the end of each center bin, $Bin_{center}+1$, and the beginning of that bin, $Bin_{center}$, as shown in Equation (11):

$$A_{center} = A(Bin_{center}+1) - A(Bin_{center}) \quad (11)$$

The end bin area, $A_{end}$, is the area between the transformed data point x+1 and the beginning of the final bin, $Bin_{end}$, as shown in Equation (12):

$$A_{end} = A(t(x+1)) - A(Bin_{end}) = (x+1) - A(Bin_{end}) \quad (12)$$

There is a special case when $Bin_{end}$ is equal to $Bin_{ini}$, and therefore there are no center bins. This case represents the high range transformation and the area to be accumulated is set equal to one, as shown in FIG. 16(b).

Using Equations (5), (6), (10), (11), and (12), it is possible to compute a look-up table, with the non-integer bins contributions and use it to accumulate an output histogram in real-time, i.e., as each input data point is acquired.

Figure 18:
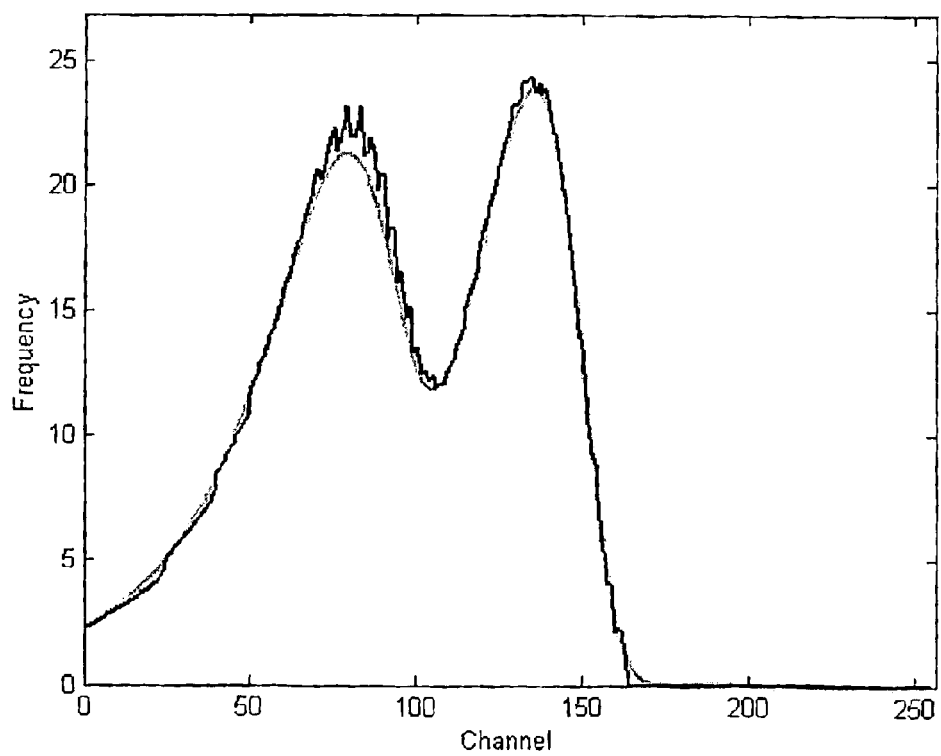
FIG. 18 shows a histogram as a solid black curve that results from using the probability-preserving signal processing operator in accordance with the present invention.

FIG. 18 shows a histogram as a solid black curve that results from using the statistical probability distribution preserving signal processing operator in accordance with the present invention, described above, and which very closely approximates the ideal curve shown as the solid gray curve. The resulting histogram has the same area as that of the initial distribution, confirming that the number of events is maintained. The use of pre-computed look-up tables makes computation time inconsequential, therefore allowing the invention to be implemented effectively in real-time.

Figure 19A:
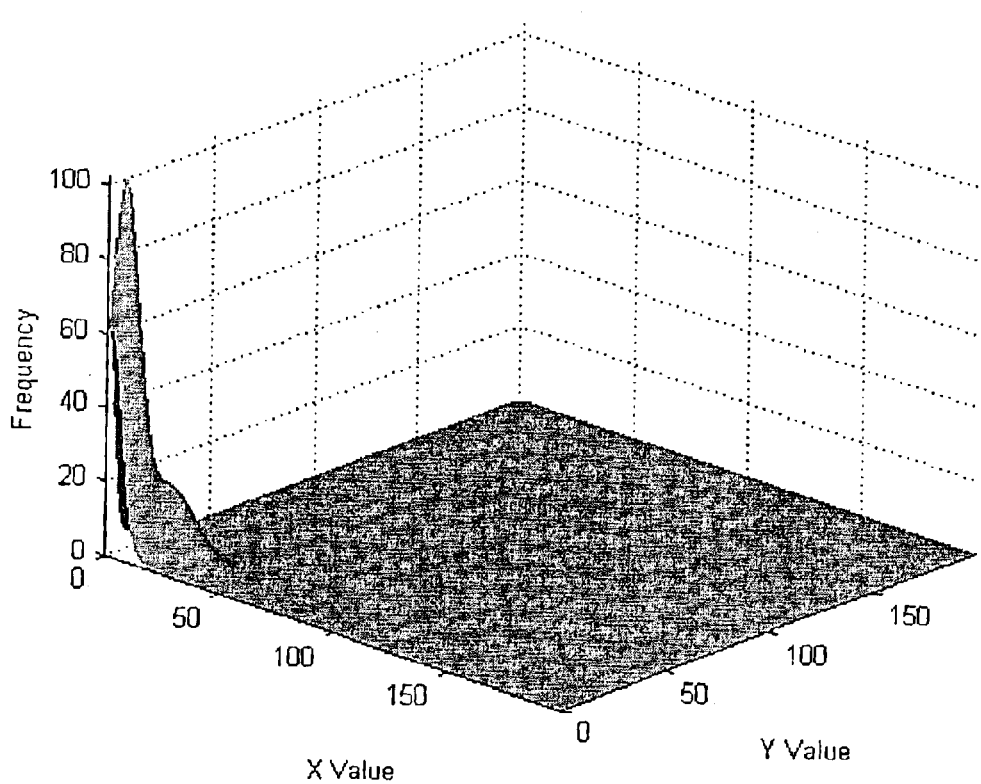
FIG. 19(a) shows a perspective view of a two-dimensional histogram.
Figure 19B:
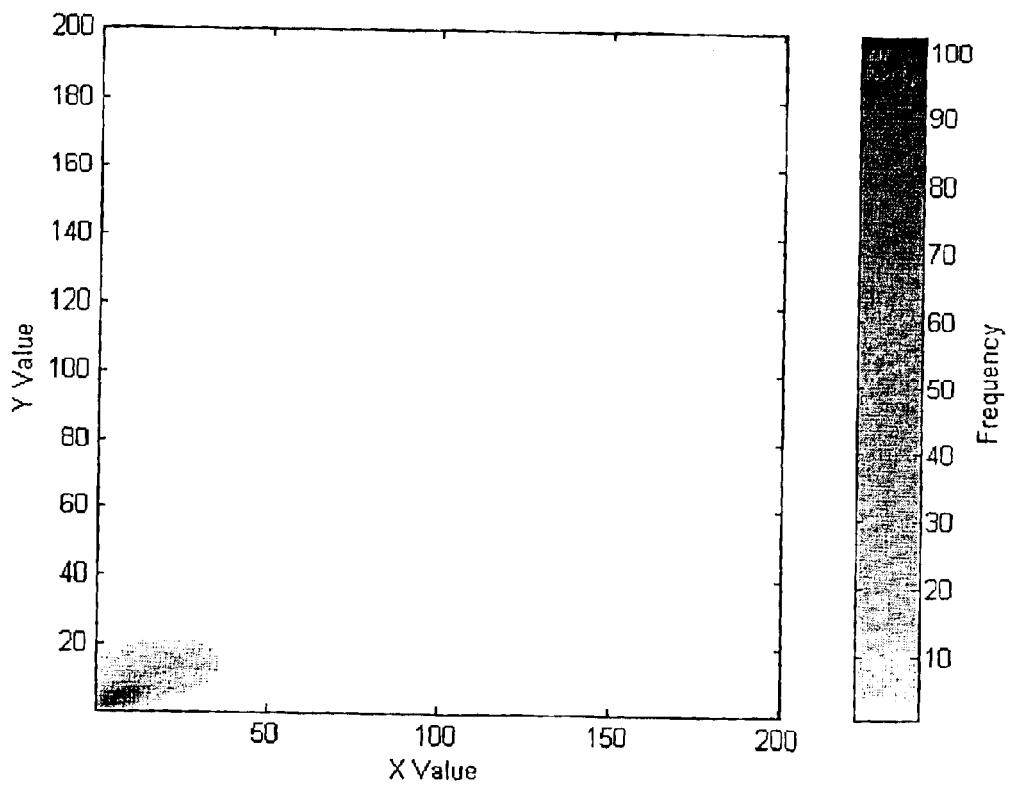
FIG. 19(b) shows a top view of the two-dimensional histogram of FIG. 19(a)
Figure 20A:
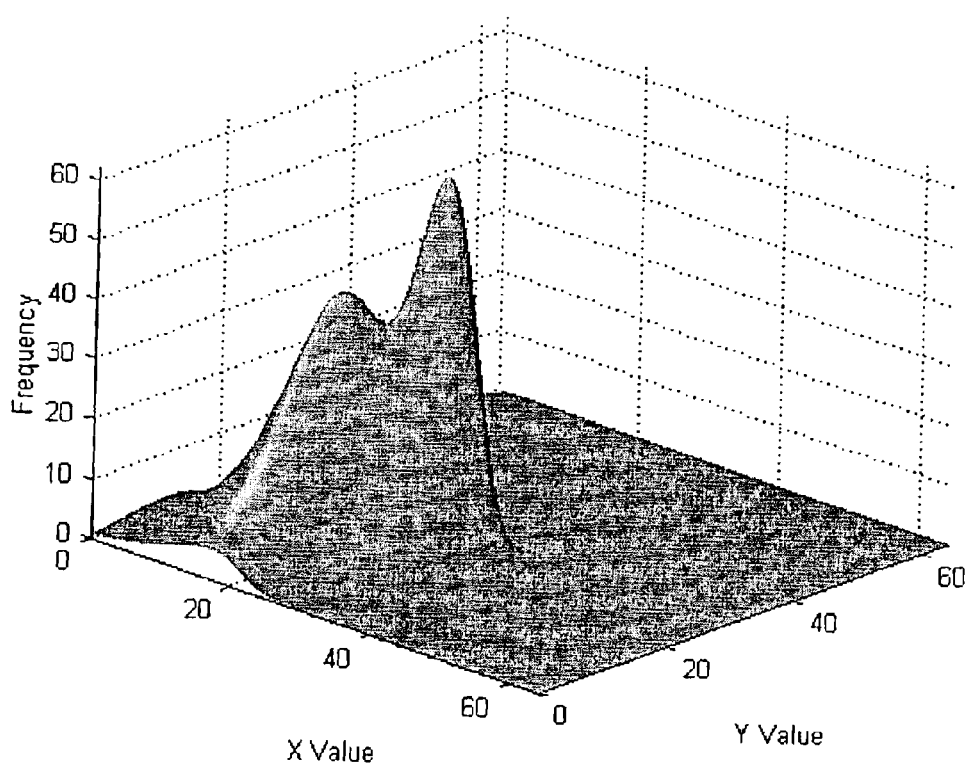
FIG. 20(a) shows a perspective view of two-dimensional ideal output transform applied to the input distribution of FIG. 19(a)
Figure 20B:
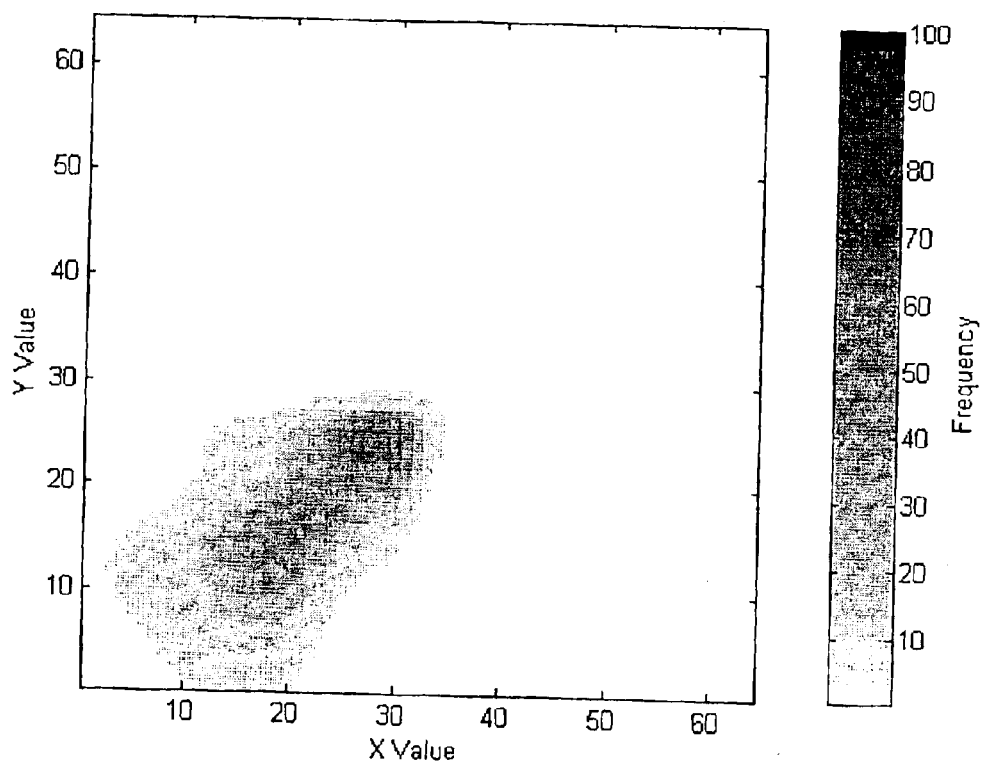
FIG. 20(b) is a top view of FIG. 20(a)
Figure 21:
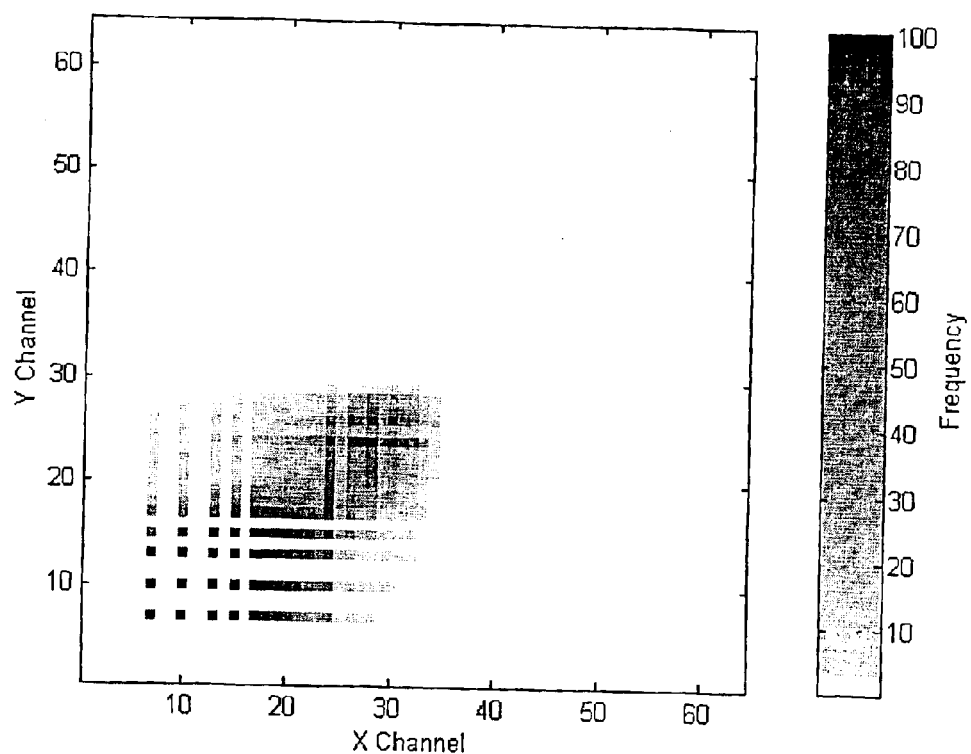
FIG. 21 is a top view of a two-dimensional transform using a conventional transform methodology that does not provide the probability distribution preservation functionality of the present invention; and FIG. 22(a)

Although the foregoing explanation of the invention presents its applicability to a one-dimensional histogram, it should be observed that the invention is equally applicable to a two-dimensional case, without a loss in generality. As an illustration, FIG. 19(a) shows a perspective view of a two-dimensional input distribution, a top view of which is shown in FIG. 19(b). FIG. 20(a) shows a perspective view of a two-dimensional ideal output transform applied to the input distribution of FIG. 19(a), while FIG. 20(b) is a top view of that ideal transform. FIG. 21 is a top view of a two-dimensional transform using the conventional methodology that does not provide the statistical probability distribution preserving functionality of the invention.

For the two-dimensional case, input data is transformed from the input domain, X, Y, to the output domain, V, W, using a given transformation $V=t(X)$ and $W=t(X)$, so that the input probability distribution, $f_{X,Y}(x,y)$ is transformed into $f_{V,W}(v,w)$. Because the transformation does not affect the probability of each event, the infinitesimal probability of any point (x,y) is the same at the output value $v=t(x)$ and $w=t(y)$. In mathematical terms this may be expressed by Equation (13) as:

$$f_{V,W}(v,w)*dv*dw=f_{X,Y}(x,y)*dx*dy \tag{13}$$

By a simple manipulation and substituting x by $t^{-1}(y)$, the relationship between the resulting probability distribution, $f_Y(y)$, and the input probability distribution, $f_X(x)$, is given in Equation (14) as:

$$f_{V,W}(v,w)=f_{X,Y}(t^{-1}(v),t^{-1}(w))*d/dv(t^{-1}(v))*d/dw(t^{-1}(w)) \tag{14}$$

where X and Y are two random variables related by the transformation $Y=t(X)$, and $t(x)$ is a monotonically increasing transformation function, whose inverse t31 1(y) has a continuous derivative on Y. Equation (2) also guarantees that the areas under the input and output probability distributions are maintained, which is an important requisite when analyzing cell populations.

Figure 22A:
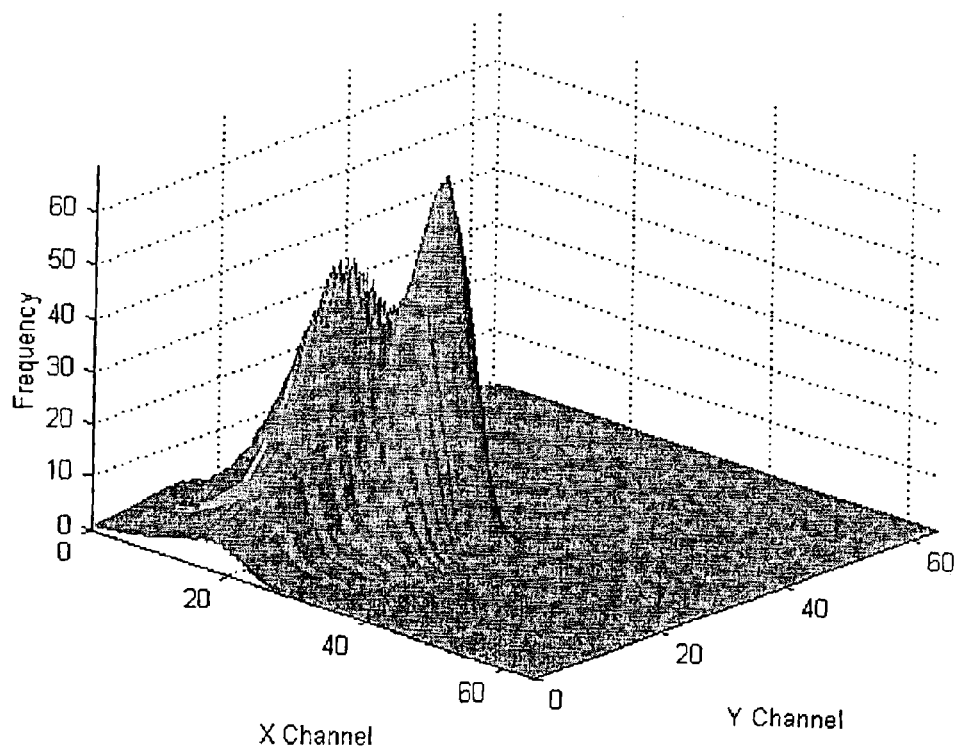
FIG. 22(b) is a perspective view and a top view respectively of the two-dimensional output transformed histogram, using the probability distribution preservation methodology in accordance with the invention as applied to the two-dimensional input distribution of FIG. 19(a).
Figure 22B:
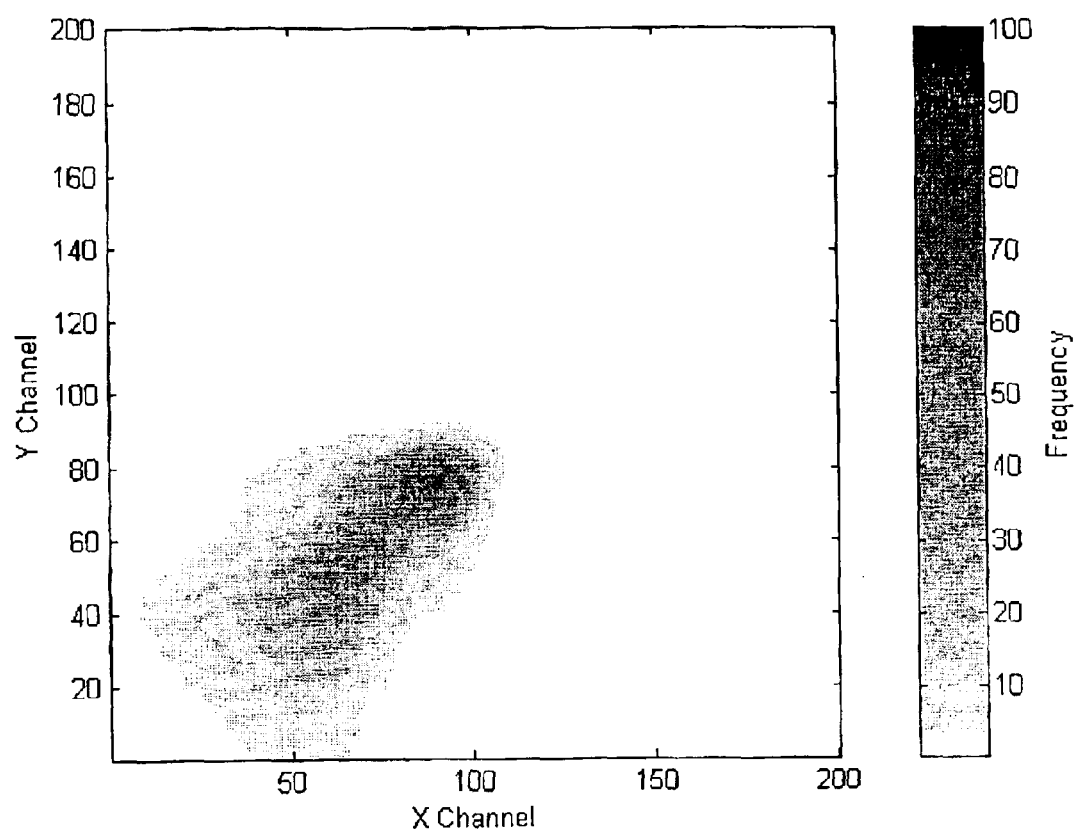

FIG. 22(a) and FIG. 22(b) is a perspective view and a top view respectively of the two-dimensional output transformed histogram, using the probability distribution preservation methodology in accordance with the invention as applied to the two-dimensional input distribution of FIG. 19(a). As can be seen from a comparison of FIGS. 22(a) and 22(b) with the ideal transform characteristic of FIGS. 20(a) and 20(b), the two are substantially the same.

As will be appreciated from the foregoing description, the above-described shortcomings of conventional signal processing mechanisms used to process histograms of data, particularly that representative of biological cell populations, including human blood cells that have been subjected to flow cytometry processing, are effectively obviated in accordance with the data mapping scheme of the present invention, which effectively preserves statistical probability distribution characteristics of the original data, that would otherwise be removed or lost in the course of expanding the dynamic range of a quantized histogram data set through the use of a conventional log transformation. With this new approach to expanding the dynamic range of a data histogram, the need for filtering becomes a non-issue since the binning effect is countered early in the process, thus preserving the statistical properties of the cell populations under study.

While we have shown and described an embodiment in accordance with the present invention, it is to be understood that the same is not limited thereto but is susceptible to numerous changes and modifications as known to a person skilled in the art. We therefore do not wish to be limited to the details shown and described herein, but intend to cover all such changes and modifications as are obvious to one of ordinary skill in the art.

What is claimed is:

1. A method of expanding the dynamic range of a set of data representative of prescribed physical phenomena comprising the steps of:
   (a) providing a dynamic range transform operator that is effective to expand the dynamic range of data applied thereto while retaining statistical distributions of said physical phenomena, producing an expanded dynamic range representation of said data that is effectively free of artifacts; and
   (b) processing said set of data in accordance with said dynamic range transform operator provided in step (a), so as to expand the dynamic range of said set of data while retaining statistical distributions of said physical phenomena, producing an expanded dynamic range representation of said set of data that is effectively free of artifacts.

2. The method according to claim 1, wherein said data is representative of a biological cell population.

3. The method according to claim 2, wherein said dynamic range transform operator has a transform characteristic derived in accordance with an inverse transformation of the domain of said data and enumerating cell populations by means of input events.

4. The method according to claim 1, wherein said data is representative of the output of a flow cytometer system.

5. The method according to claim 1, wherein step (b) comprises expanding the dynamic range of said data in accordance with a logarithmic transform operator.

6. The method according to claim 1, wherein said dynamic range transform operator employs one of a uniform approximation, a linear approximation, and a polynomial approximation of probability distribution of said data.

7. The method according to claim 1, wherein said dynamic range transform operator is operative to transform said data effectively in real time.

8. The method according to claim 1, wherein step (a) comprises providing an input histogram of said data, and step (b) comprises expanding the dynamic range of said input histogram to produce an output histogram in accordance with a transformation operator, that is operative to accumulate said output histogram in a non-integer and multi-channel fashion, wherein, for a respective data value of said input histogram, plural output histogram channels are accumulated in non-integer amounts.

9. The method according to claim 8, wherein step (b) comprises accumulating said output histogram using a look-up table containing pre-computed non-integer channel contributions indexed by input channel.

10. The method according to claim 8, wherein said output histogram channels have integer boundaries, and wherein for a respective data value of said input histogram, areas of plural output histogram channels associated therewith sum to a prescribed value.

11. The method according to claim 10, wherein said prescribed value equals one.

12. The method according to claim 1, wherein step (a) comprises providing an input histogram of said data, and step (b) comprises expanding the dynamic range of said input histogram to produce an output histogram in accordance with a statistical probability-preserving dynamic range transformation operator, that is operative to accumulate said output histogram in a non-integer and multi-channel fashion, wherein, for a respective data range of said input histogram, plural output histogram channels are accumulated in non-integer overlapping amounts, that are effective to cause a spreading of input data into plural non-integer bins, producing overlapping contributions between contiguous data points that fill in discontinuities and are exclusive of the presence of spikes in said output histogram.

13. A method of processing a digital input histogram of input data representative of a biological cell population as produced by a flow cytometer system, said method comprising the steps of:

(a) processing said digital input histogram in accordance with a prescribed dynamic range transform operator that is effective to produce an output histogram in which the domain of said input data has been expanded into an increased number of output channels; and (b) causing said prescribed dynamic range transform operator to effectively retain statistical probability distributions of said biological cell population in the course of accumulating said input data into said output channels of said output histogram in a non-integer and multi-channel fashion, such that, for a respective data range of said input histogram, plural output histogram channels are accumulated in non-integer amounts, causing a spreading of input data into plural non-integer output histogram channels, thereby producing overlapping contributions between contiguous data points and resulting in an expanded dynamic range output histogram that is effectively free of binning artifacts.

14. The method according to claim 13, wherein said output histogram channels have integer boundaries, and wherein for a respective data value of said input histogram, areas of plural output histogram channels associated therewith sum to a value of one.

15. The method according to claim 13, wherein said prescribed dynamic range transform operator comprises a logarithmic transform operator.

16. The method according to claim 13, wherein said prescribed dynamic range transform operator employs one of a uniform approximation, a linear approximation, and a polynomial approximation of probability distribution of said data.

17. The method according to claim 13, wherein said prescribed dynamic range transform operator is operative to accumulate said input data into said output histogram effectively in real time.

18. The method according to claim 17, wherein step (b) comprises accumulating said output histogram using a look-up table containing pre-computed non-integer channel contributions indexed by input channel.

19. A method for using a data processing system wherein a digital input histogram of input data representative of a physical component population is processed in accordance with a prescribed dynamic range transform operator that is effective to produce an output histogram wherein the improvement comprises:

a prescribed dynamic range transform operator comprising a statistical probability-preserving transformation operator, that is operative to accumulate said output histogram in a non-integer and multi-channel fashion, wherein, for a respective input channel of said input histogram, plural output histogram channels are accumulated in non-integer overlapping amounts, that are effective to cause a spreading of input data into plural non-integer bins of said output histogram, producing overlapping contributions between contiguous data points in said output histogram that fill in discontinuities and are exclusive of the presence of spikes therein.

20. The improvement according to claim 19, wherein said input data is representative of the output of a flow cytometer system.

* * * * *